US008257286B2

(12) United States Patent
Meyer et al.

(10) Patent No.: US 8,257,286 B2
(45) Date of Patent: Sep. 4, 2012

(54) SAFETY CONNECTOR APPARATUS

(75) Inventors: Ann Meyer, Shrewsbury, MA (US);
Malcolm Bock, Medfield, MA (US)

(73) Assignee: Tyco Healthcare Group LP, Mansfield, MA (US)

(*) Notice: Subject to any disclaimer, the term of this patent is extended or adjusted under 35 U.S.C. 154(b) by 1238 days.

(21) Appl. No.: 11/533,924

(22) Filed: Sep. 21, 2006

(65) Prior Publication Data
US 2008/0077063 A1    Mar. 27, 2008

(51) Int. Cl.
A61H 7/00    (2006.01)
F16L 35/00    (2006.01)

(52) U.S. Cl. ........................................ 601/148; 285/328

(58) Field of Classification Search ............... 601/41, 601/44, 148–153; 285/374, 399, 190, 913, 285/14, 144.1, 148.16, 304, 328, 91, 419; 128/912
See application file for complete search history.

(56) References Cited

U.S. PATENT DOCUMENTS

| 2,280,485 | A |   | 4/1942  | Harris          |        |
|-----------|---|---|---------|-----------------|--------|
| 2,694,393 | A |   | 11/1954 | Simpson         |        |
| 2,694,395 | A |   | 11/1954 | Brown           |        |
| 2,893,395 | A |   | 7/1959  | Buck            |        |
| 3,057,001 | A |   | 10/1962 | Rapata          |        |
| 3,097,866 | A | * | 7/1963  | Iversen         | 285/18 |
| 3,287,031 | A | * | 11/1966 | Simmons et al.  | 285/27 |
| 3,454,006 | A |   | 7/1969  | Langdon         |        |
| 3,625,212 | A |   | 12/1971 | Rosenberg et al.|        |
| 3,728,875 | A |   | 4/1973  | Hartigan et al. |        |
| 3,733,577 | A |   | 5/1973  | Hammond         |        |
| 3,834,388 | A |   | 9/1974  | Sauer           |        |
| 4,013,069 | A |   | 3/1977  | Hasty           |        |
| 4,029,087 | A |   | 6/1977  | Dye et al.      |        |
| 4,030,488 | A |   | 6/1977  | Hasty           |        |
| 4,066,084 | A |   | 1/1978  | Tillander       |        |
| 4,091,804 | A |   | 5/1978  | Hasty           |        |
| 4,149,529 | A | * | 4/1979  | Copeland et al. | 601/17 |
| 4,150,673 | A |   | 4/1979  | Watt            |        |
| 4,156,425 | A |   | 5/1979  | Arkans          |        |
| 4,198,961 | A |   | 4/1980  | Arkans          |        |
| 4,207,875 | A |   | 6/1980  | Arkans          |        |
| 4,207,876 | A |   | 6/1980  | Annis           |        |
| 4,211,439 | A |   | 7/1980  | Moldestad       |        |
| 4,253,449 | A | * | 3/1981  | Arkans et al.   | 601/152|
| 4,280,485 | A |   | 7/1981  | Arkans          |        |

(Continued)

FOREIGN PATENT DOCUMENTS

BE    893623 A1    10/1982

(Continued)

OTHER PUBLICATIONS

The Kendall Company, "The New SCD Compression Sleeve", Aug. 1993, pp. 1-2.

(Continued)

*Primary Examiner* — Justine Yu
*Assistant Examiner* — Valerie L Skorupa
(74) *Attorney, Agent, or Firm* — Thomas M. Johnston, Esq.

(57) ABSTRACT

A connector apparatus includes first and second mating connectors that can be joined to make a fluid connection. The connectors are constructed to discriminate improper connectors so that no fluid tight connection can be formed with improper connectors. The connector apparatus can be used with a system for compression therapy to prevent deep vein thrombosis.

13 Claims, 24 Drawing Sheets

U.S. PATENT DOCUMENTS

| | | | |
|---|---|---|---|
| 4,280,723 A * | 7/1981 | Moldestad | 285/376 |
| 4,369,781 A | 1/1983 | Gilson et al. | |
| 4,580,816 A | 4/1986 | Campbell et al. | |
| 4,619,640 A | 10/1986 | Potolsky et al. | |
| 4,762,504 A | 8/1988 | Michaels et al. | |
| 4,790,567 A | 12/1988 | Kawano et al. | |
| 4,795,429 A | 1/1989 | Feldstein | |
| 4,804,208 A | 2/1989 | Dye | |
| D300,177 S | 3/1989 | Bellotti et al. | |
| 4,824,145 A | 4/1989 | Carlsson | |
| RE32,939 E | 6/1989 | Gardner et al. | |
| 4,867,699 A | 9/1989 | Oda et al. | |
| 4,872,736 A | 10/1989 | Myers et al. | |
| 4,887,849 A * | 12/1989 | Briet | 285/91 |
| 4,988,062 A | 1/1991 | London | |
| 5,007,411 A | 4/1991 | Dye | |
| 5,009,252 A * | 4/1991 | Faughn | 137/614.04 |
| 5,022,387 A | 6/1991 | Hasty | |
| 5,031,604 A | 7/1991 | Dye | |
| 5,041,025 A | 8/1991 | Haitmanek | |
| 5,062,550 A | 11/1991 | Singh | |
| 5,117,812 A | 6/1992 | McWhorter | |
| 5,123,677 A | 6/1992 | Kreczko et al. | |
| 5,156,603 A | 10/1992 | Olsen | |
| 5,165,728 A | 11/1992 | Mayer | |
| 5,176,406 A | 1/1993 | Straghan | |
| 5,186,163 A | 2/1993 | Dye | |
| 5,190,534 A | 3/1993 | Kendell | |
| 5,215,538 A | 6/1993 | Larkin | |
| 5,217,384 A | 6/1993 | Merten et al. | |
| 5,219,185 A | 6/1993 | Oddenino | |
| 5,224,932 A | 7/1993 | Lappas | |
| 5,240,289 A * | 8/1993 | Gottling et al. | 285/24 |
| 5,249,830 A | 10/1993 | Calmettes et al. | |
| 5,263,945 A | 11/1993 | Byrnes et al. | |
| 5,273,254 A | 12/1993 | McNaughton et al. | |
| 5,285,776 A | 2/1994 | Bertram | |
| 5,330,366 A | 7/1994 | Tsuji et al. | |
| 5,354,260 A | 10/1994 | Cook | |
| 5,370,423 A | 12/1994 | Guest | |
| 5,383,894 A | 1/1995 | Dye | |
| 5,387,110 A | 2/1995 | Kantner et al. | |
| D357,736 S | 4/1995 | Dye | |
| 5,435,009 A | 7/1995 | Schild et al. | |
| 5,437,610 A | 8/1995 | Cariapa et al. | |
| 5,443,289 A | 8/1995 | Guest | |
| D363,988 S | 11/1995 | Dye | |
| 5,478,119 A * | 12/1995 | Dye | 285/26 |
| 5,507,732 A | 4/1996 | McClure et al. | |
| 5,509,911 A | 4/1996 | Cottone, Sr. et al. | |
| 5,518,416 A | 5/1996 | Kantner et al. | |
| 5,546,934 A | 8/1996 | Kaigler et al. | |
| D375,357 S | 11/1996 | Silver | |
| 5,575,762 A | 11/1996 | Peeler et al. | |
| 5,588,954 A | 12/1996 | Ribando et al. | |
| 5,588,955 A | 12/1996 | Johnson, Jr. et al. | |
| 5,591,143 A | 1/1997 | Trombley, III et al. | |
| 5,591,200 A | 1/1997 | Cone et al. | |
| 5,626,556 A | 5/1997 | Tobler et al. | |
| 5,637,102 A | 6/1997 | Tolkoff et al. | |
| 5,695,224 A | 12/1997 | Grenier | |
| 5,711,757 A | 1/1998 | Bryant | |
| 5,725,425 A | 3/1998 | Rump et al. | |
| 5,725,485 A | 3/1998 | Ribando et al. | |
| 5,725,511 A | 3/1998 | Urrutia | |
| 5,735,841 A | 4/1998 | Bourguignon et al. | |
| 5,743,755 A | 4/1998 | Aoki | |
| 5,782,808 A | 7/1998 | Folden | |
| 5,810,398 A | 9/1998 | Matkovich | |
| 5,843,007 A | 12/1998 | McEwen et al. | |
| 5,876,359 A | 3/1999 | Bock et al. | |
| 5,897,142 A | 4/1999 | Kulevsky | |
| 5,947,937 A | 9/1999 | Urrutia et al. | |
| 5,951,502 A | 9/1999 | Peeler et al. | |
| 5,971,927 A | 10/1999 | Mine | |
| 5,971,972 A | 10/1999 | Rosenbaum | |
| 5,988,704 A | 11/1999 | Ryhman | |
| 5,989,204 A | 11/1999 | Lina | |
| 5,989,240 A | 11/1999 | Strowe | |
| 6,062,244 A | 5/2000 | Arkans | |
| 6,113,572 A | 9/2000 | Gailey et al. | |
| 6,126,610 A | 10/2000 | Rich | |
| 6,129,688 A | 10/2000 | Arkans | |
| 6,145,539 A | 11/2000 | Wilcox et al. | |
| 6,152,495 A | 11/2000 | Hoffmann et al. | |
| 6,156,025 A | 12/2000 | Niedospial, Jr. | |
| 6,165,149 A | 12/2000 | Utterberg et al. | |
| 6,193,697 B1 | 2/2001 | Jepson et al. | |
| 6,231,532 B1 | 5/2001 | Watson et al. | |
| 6,238,230 B1 | 5/2001 | Sadler et al. | |
| 6,257,626 B1 | 7/2001 | Campau | |
| 6,257,627 B1 | 7/2001 | Fujiwara et al. | |
| 6,296,617 B1 | 10/2001 | Peeler et al. | |
| D450,838 S | 11/2001 | Cise et al. | |
| 6,319,215 B1 | 11/2001 | Manor et al. | |
| 6,402,207 B1 | 6/2002 | Segal et al. | |
| 6,423,053 B1 | 7/2002 | Lee | |
| 6,436,064 B1 | 8/2002 | Kloecker | |
| 6,440,093 B1 | 8/2002 | McEwen et al. | |
| 6,468,237 B1 | 10/2002 | Lina | |
| 6,523,861 B1 | 2/2003 | Clancy et al. | |
| 6,537,099 B2 | 3/2003 | Herlinger et al. | |
| 6,544,202 B2 | 4/2003 | McEwen et al. | |
| 6,547,284 B2 | 4/2003 | Rose et al. | |
| 6,581,906 B2 | 6/2003 | Pott et al. | |
| 6,592,534 B1 | 7/2003 | Rutt et al. | |
| 6,612,624 B1 | 9/2003 | Segal et al. | |
| 6,620,119 B1 | 9/2003 | Utterberg et al. | |
| 6,629,941 B1 | 10/2003 | Ishibashi et al. | |
| 6,652,509 B1 | 11/2003 | Helgren et al. | |
| 6,666,839 B2 | 12/2003 | Utterberg et al. | |
| 6,802,836 B2 | 10/2004 | Bouphavichith et al. | |
| 6,802,855 B2 | 10/2004 | Ellingboe et al. | |
| 6,827,728 B2 | 12/2004 | Ellingboe et al. | |
| 6,949,084 B2 | 9/2005 | Marggi et al. | |
| 7,007,983 B2 | 3/2006 | Arosio | |
| 7,137,654 B2 | 11/2006 | Segal et al. | |
| 7,140,592 B2 | 11/2006 | Phillips | |
| 7,240,926 B2 | 7/2007 | Dalle et al. | |
| 7,347,853 B2 | 3/2008 | DiFiore et al. | |
| 7,484,769 B2 | 2/2009 | Domash et al. | |
| 7,490,620 B2 | 2/2009 | Tesluk et al. | |
| 2002/0096883 A1 | 7/2002 | Youssefifar | |
| 2003/0001387 A1* | 1/2003 | Tawara et al. | 285/328 |
| 2003/0045153 A1 | 3/2003 | Yamawaki | |
| 2003/0075923 A1 | 4/2003 | Lepoutre | |
| 2003/0144647 A1 | 7/2003 | Miyahara | |
| 2003/0191445 A1 | 10/2003 | Wallen et al. | |
| 2003/0191453 A1 | 10/2003 | Velez et al. | |
| 2004/0030373 A1 | 2/2004 | Ellingboe et al. | |
| 2004/0034324 A1 | 2/2004 | Seese et al. | |
| 2004/0039317 A1 | 2/2004 | Souney et al. | |
| 2004/0111078 A1 | 6/2004 | Miyahara | |
| 2004/0201216 A1 | 10/2004 | Segal et al. | |
| 2004/0227120 A1 | 11/2004 | Raybuck | |
| 2005/0085794 A1* | 4/2005 | Denoth et al. | 604/533 |
| 2005/0090805 A1 | 4/2005 | Shaw et al. | |
| 2005/0143682 A1 | 6/2005 | Cook et al. | |
| 2005/0184264 A1* | 8/2005 | Tesluk et al. | 251/148 |
| 2005/0234407 A1 | 10/2005 | Spohn et al. | |
| 2006/0004245 A1 | 1/2006 | Pickett et al. | |
| 2006/0025751 A1 | 2/2006 | Roy et al. | |
| 2006/0116660 A1 | 6/2006 | Cawley | |
| 2006/0189961 A1 | 8/2006 | Miyahara | |
| 2007/0020752 A1 | 1/2007 | Russell et al. | |
| 2007/0060898 A1 | 3/2007 | Shaughnessy et al. | |
| 2007/0073270 A1 | 3/2007 | Christensen et al. | |
| 2007/0088327 A1 | 4/2007 | Guala | |
| 2008/0228125 A1 | 9/2008 | Brugger et al. | |
| 2008/0300542 A1 | 12/2008 | Kitani et al. | |

FOREIGN PATENT DOCUMENTS

| | | |
|---|---|---|
| DE | 2907832 A1 | 9/1980 |
| DE | 20301094 U1 | 4/2003 |
| DE | 10333118 B4 | 2/2008 |
| EP | 0151519 A1 | 8/1985 |
| EP | 0585633 A1 | 3/1994 |

| | | | |
|---|---|---|---|
| EP | 0634190 A2 | 1/1995 | |
| EP | 0832666 A2 | 4/1998 | |
| EP | 0880978 A2 | 12/1998 | |
| FR | 1171861 A | 1/1959 | |
| FR | 2863162 A1 | 6/2005 | |
| GB | 2343723 | 5/2000 | |
| WO | 8100053 A1 | 1/1981 | |
| WO | 9012606 A2 | 11/1990 | |
| WO | 9822175 A1 | 5/1998 | |
| WO | 0123026 A1 | 4/2001 | |
| WO | 2004073778 A1 | 9/2004 | |

OTHER PUBLICATIONS

The Kendall Company, "Vascular Therapy Products Catalog", Jan. 1996, pp. 7-5 to 7-6.

Tyco Healthcare Kendall, "Prevention Gets Personal", Mar. 2001, pp. 1-4.

Tyco Healthcare Kendall, "SCD Response Sequential Compression System Catalog", Mar. 2000, pp. 1-2.

Tyco Healthcare Kendall, "SCD Soft Sleeve Catalog", Apr. 2001, pp. 1-2.

Kendall SCD, "Sequential Compression Sleeves," Jan. 1993, pp. 1-6.

Partial European Search Report, Application No. 07116839.7, dated Dec. 20, 2007, 6 pages.

Extended European Search Report issued in Application No. 07116839.7, dated Apr. 23, 2008, 26 pages.

European Search Report dated Jun. 9, 2010 from related case EP 09166601.6, 7 pages.

Office action issued Apr. 21, 2010 in related U.S. Appl. No. 11/852,841, 7 pgs.

Response filed Jul. 1, 2010 to Office Action dated Apr. 21, 2010 from related U.S. Appl. No. 11/852,841, 8 pgs.

Office action dated Sep. 30, 2010 from U.S. Appl. No. 11/852,841, 6 pages.

European Search Report regarding related application serial No. EP 10168082.5 dated Aug. 30, 2010, 7 pages.

European Search Report regarding related application serial No. EP 10168087.4 dated Aug. 30, 2010, 6 pages.

Response filed Dec. 21, 2010 to Office Action dated Sep. 30, 2010 from related U.S. Appl. No. 11/852,841; 8 pgs.

Office action issued Mar. 16, 2011 in related U.S. Appl. No. 11/852,841; 8 pgs.

Response filed Jun. 16, 2011 to Office Action dated Mar. 16, 2011 from related U.S. Appl. No. 11/852,841. 7 pgs.

European Search Report regarding related application serial No. EP 10185364.6 dated Sep. 5, 2011—7 pgs.

* cited by examiner

SAFETY CONNECTOR APPARATUS

TECHNICAL FIELD

The present disclosure relates to safety connectors for use in medical applications, particularly for use with compression therapy devices. The present disclosure also relates to discriminating safety connector apparatus and, more particularly, to a discriminating safety connector apparatus for fluidly coupling at least two lumens capable of forming a non-leaking fluid circuit.

BACKGROUND OF THE INVENTION

In a medical environment, many devices have tubing adapted for manual connection in order to provide a fluid connection between devices or between a device and a patient including enteral feeding pumps and intravenous feeding lines. Each of these devices includes one or more connectors that a user or practitioner may inadvertently connect together. This may result in the successful connection of incompatible devices or the supply of fluid or nutrient to an improper intravenous line or a device such as an inflatable bladder used in deep vein thrombosis therapy. Successful connection of incompatible devices may harm patients or damage equipment.

When connecting a medical device to a fluid supply, a non-leaking seal must be made between compatible devices and/or fluid sources. Thus, connections must be designed to provide an adequate seal between sealing surfaces when the devices and/or supply are compatible. Typical devices have a male and female connector that, when pressed together, form a fluid tight seal. The connectors come in different sizes and shapes and typically have O-rings or gaskets to help create a fluid tight seal.

Examples of a medical device connected to a fluid supply include compression therapy devices that are wrapped around a limb to prevent peripheral edema and conditions that form blood clots such as deep vein thrombosis. These devices typically include at least one air bladder that is sized and shaped for being applied around the limb. The bladder is sequentially inflated and deflated to artificially stimulate blood flow throughout the appendage that would normally result from, for example, walking. An example of such a device that is configured for disposal about a foot is shown in U.S. Pub. No. 2005/0187499. Typically, these compression devices are connected to a tube set which provides fluid communication from a pressure source to the compression device. A controller is employed to regulate the flow of fluid from the pressure source to the compression device.

The compression device, tube set and controller each contain connections for connecting and disconnecting the compression device from the pressure source. It is desirable to avoid erroneous connection of a medical device other than the compression device, for example an intravenous needle, to the pressure source.

SUMMARY OF THE INVENTION

The present invention is directed to a compression therapy device for use with a source of air pressure having a male connector. The compression therapy device comprises at least one air bladder sized and shaped for being applied to an appendage of a patient and a female connector in fluid communication with the air bladder. The female connector is adapted for connection to the male connector for inflating the air bladder to apply compression to the appendage. The female connector comprises a receptacle having an open outer end and being sized and shaped for receiving at least a portion of the male connector therein, a stop generally at an inner end of the receptacle for engaging the mating connector upon insertion in the receptacle to set the maximum distance of insertion of the male connector, and a sealing member located in the receptacle at a location spaced from the shoulder toward the open outer end of the receptacle. Upon insertion of the male connector into the receptacle, a non-sealing surface of the male connector engages the sealing member in non-sealing relation, passes by the sealing member and brings a sealing surface of the male connector into sealing relation with the sealing member for preventing inadvertent sealing connection with a connector other than the male connector.

The present invention is also directed to a tube set for use in making discriminating fluid connection between a source of fluid and a fluid-receiving object. The tube set comprises a tube, a first connector connected to the tube at a first end thereof. The first connector includes at least one sealing surface and at least one non-sealing surface. The non-sealing surface is located closer to a free end of the first connector than the sealing surface. The non-sealing surface is sized and shaped for engaging a sealing surface of another connector simultaneously at least at three points, each point being spaced at least about 90 degrees from the other two points, without forming a fluid seal with the sealing surface.

The present invention is also directed to a compression therapy device controller for controlling the supply of fluid from a source of pressurized fluid to a compression therapy device. The controller comprises a housing, a fluid port in the housing and a connector for the fluid port having at least one sealing surface and at least one non-sealing surface. The non-sealing surface is located closer to a free end of the connector than the sealing surface. The non-sealing surface is sized and shaped for engaging a sealing surface of another connector simultaneously at least at three points, each point being spaced at least 90 degrees from the other two points without forming a fluid seal with the sealing surface.

The present invention is also directed to a system for providing vascular compression. The system comprises a controller, a tube set, and a compression therapy device. The controller includes a first connector having at least one sealing surface and at least one non-sealing surface. The non-sealing surface is located closer to a free end of the first connector than the sealing surface. The compression therapy device includes a second connector including a sealing member. The tube set includes a tube and a third connector at one end of the tube having a sealing member adapted to engage the non-sealing surface and sealing surface of the first connector of the controller upon connection of the first and third connectors. The tube set further comprises a fourth connector having at least one sealing surface and at least one non-sealing surface located closer to a free end of the fourth connector than the sealing surface. The non-sealing surface of the fourth connector is adapted to engage the sealing member of the second connector upon connection of the second and fourth connectors.

The present invention is also directed to a connector apparatus comprising a first connector having an internal sealing surface and an array of protrusions on an outer surface. Each protrusion is at least one of circumferentially spaced and axially spaced of the first connector from the other protrusions for defining fluid flow paths on an outer surface of the first connector for preventing fluid tight connection of any tube in which the outer surface of the first connector may be received. The connector apparatus further comprises a second connector, adapted for sealing engagement with the internal sealing surface of the first connector for forming a fluid tight connection with the first connector.

The present invention is also directed to a method of connecting a first device to a second device. The method comprises providing a first device having a first connector, the first connector including an attachment portion and a coupling portion, wherein the coupling portion includes a sealing surface at a second end and a non-sealing surface at a first end. The method further comprises providing a second device having a second connector, the second connector including a sealing member configured to receive the coupling portion. The method further comprises attaching the first connector to the second connector and positioning the first and second connectors such that the sealing surface of the coupling portion contacts the sealing member of the second portion forming a fluid tight seal between the first and second connectors.

The present invention is also directed to a connector apparatus comprising a first connector having an attachment portion and a coupling portion. The coupling portion has at least one sealing surface and at least one non-sealing surface. The connector apparatus further comprises a second connector having an attachment portion and at least one sealing member and is configured to receive the coupling portion. The at least one sealing member slides beyond the at least one non-sealing surface to create a fluid tight seal between the at least one sealing surface and the at least one sealing member.

The present invention is also directed to a connector apparatus comprising a first connector having a housing, an attachment portion, and a coupling portion. The coupling portion includes a key. The connector apparatus further comprises a second connector having a housing and an attachment portion. The housing has a mating cavity formed therein for capturing the key of the first connector when the first and second connectors are mated in sealing relation.

Other objects and features will be in part apparent and in part pointed out hereinafter.

BRIEF DESCRIPTION OF THE DRAWINGS

Embodiments of the present disclosure are described herein below with reference to the drawings wherein.

Corresponding reference characters indicate corresponding parts throughout the drawings.

DESCRIPTION OF THE PREFERRED EMBODIMENTS

Figure 1:
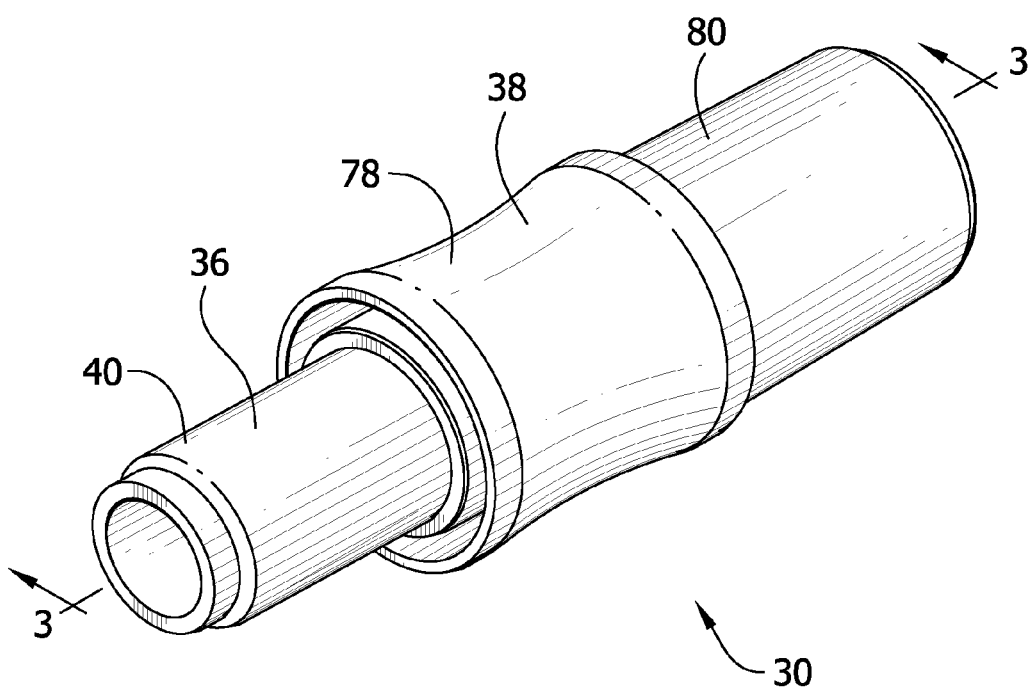
FIG. 1 is a perspective of a connector apparatus with a first and second connector of the connector apparatus engaged.
Figure 2:
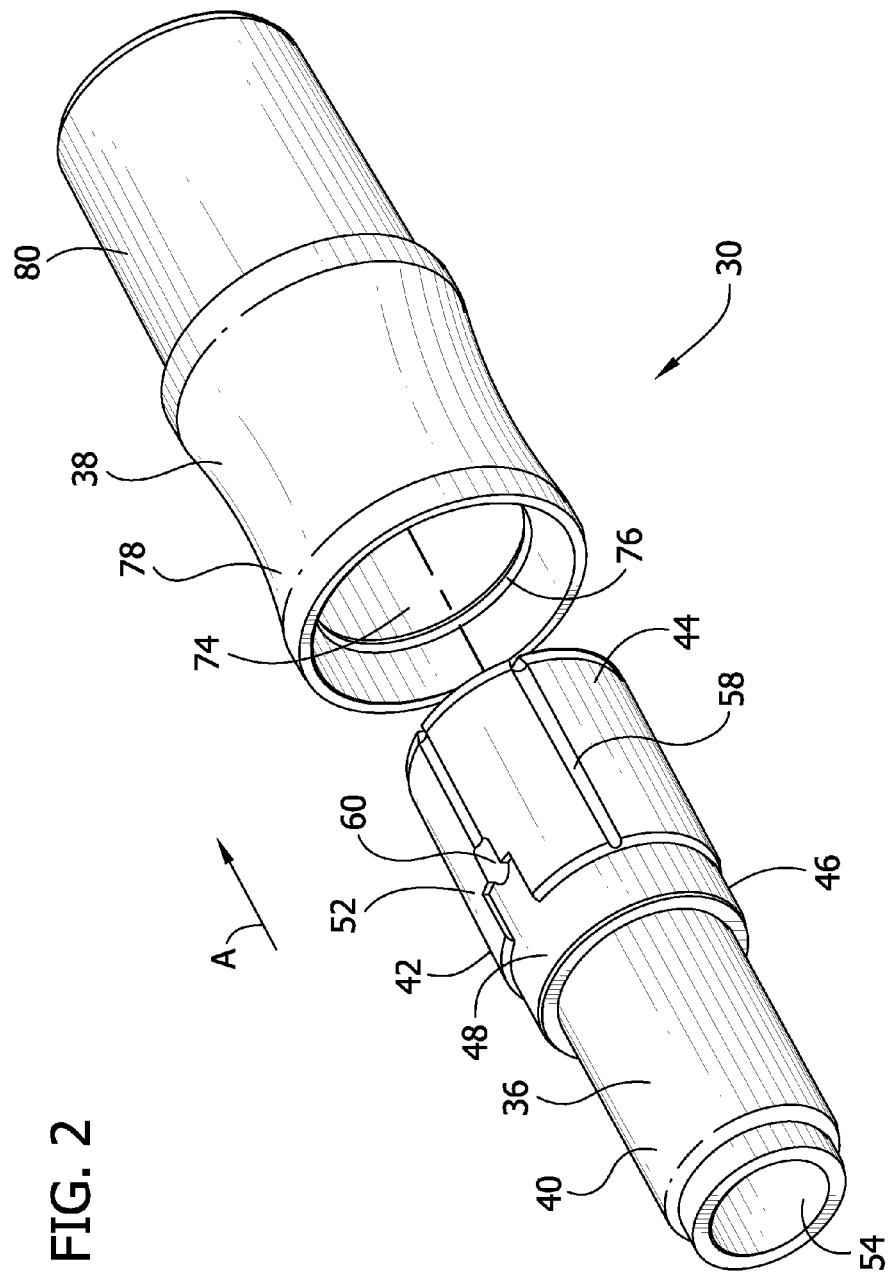
FIG. 2 is a perspective of the connector apparatus with the first and second connector separated.
Figure 20:
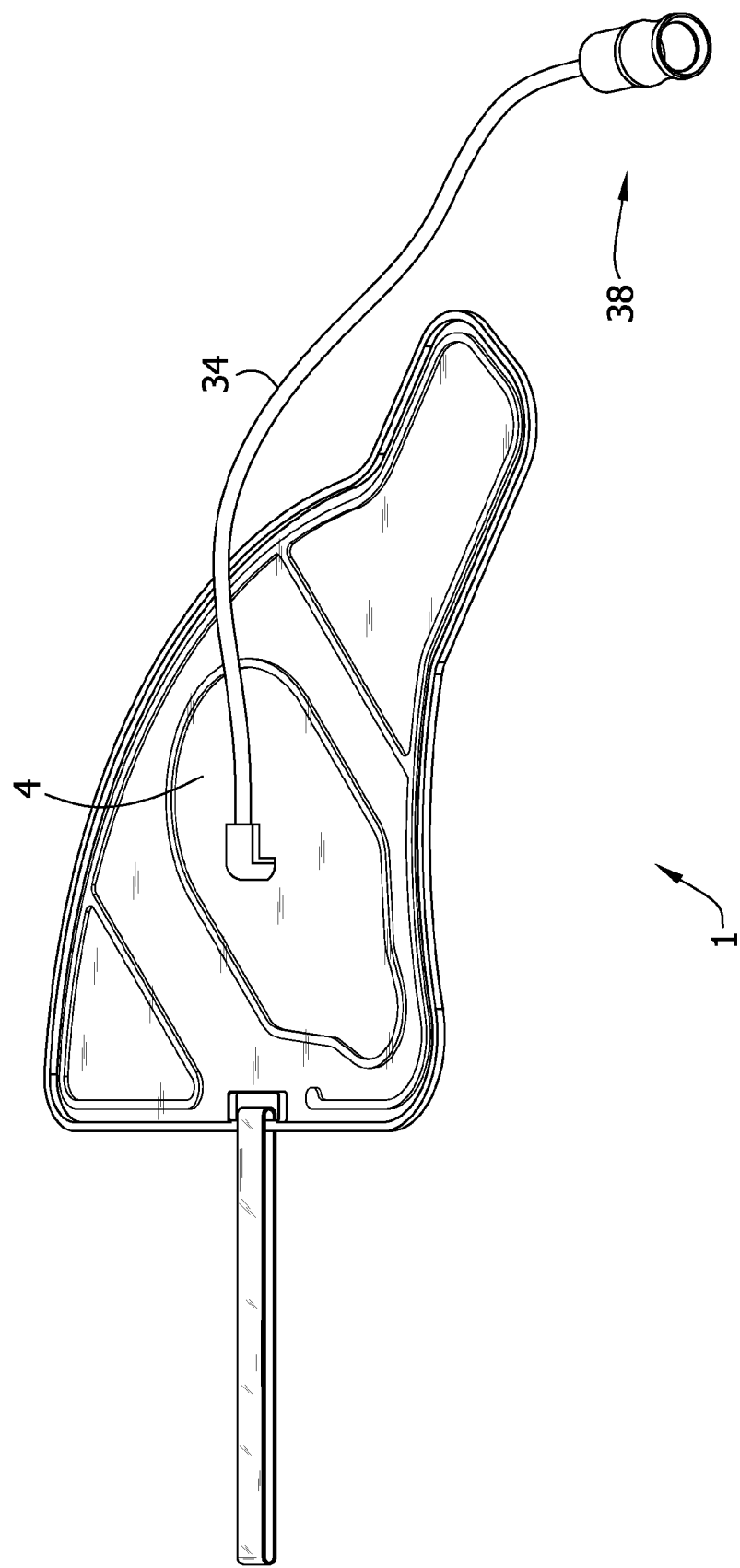
FIG. 20 is a perspective of a compression therapy device showing an inflatable bladder and an enlarged view of the connector.

Referring now to the drawings, a connector apparatus 30 constructed according to the principles of the present invention is shown in FIGS. 1 and 2 to comprise a first connector 36 and a second connector 38. As described more fully hereinafter, the first and second connectors 36, 38 are capable of discriminating connection to preferentially achieve fluid-tight connection of the connectors, and avoid fluid-tight connection with non-complying connectors. The connector system 30 may be used, for example, to connect a controller 2 to a compression therapy device 1 for cyclically supplying air pressure to a bladder 4 of the device (see, FIGS. 20 and 21). The compression therapy device 1 illustrated in FIG. 20 is of the type which is applied to the foot for repeatedly compressing the foot to force blood out of the foot and discourage pooling of blood in the foot that can lead to clots. Although a foot compression therapy device 1 is illustrated, other types of compression therapy devices can be employed, such as those that are applied to the leg. Other examples of foot and leg devices are disclosed in U.S. Pat. Nos. 5,626,556 and 5,795,312. Moreover, the connector apparatus 30 can be used for other types of medical fluid connections such as the connection of an enteral feeding bag to a patient.

Figure 21:
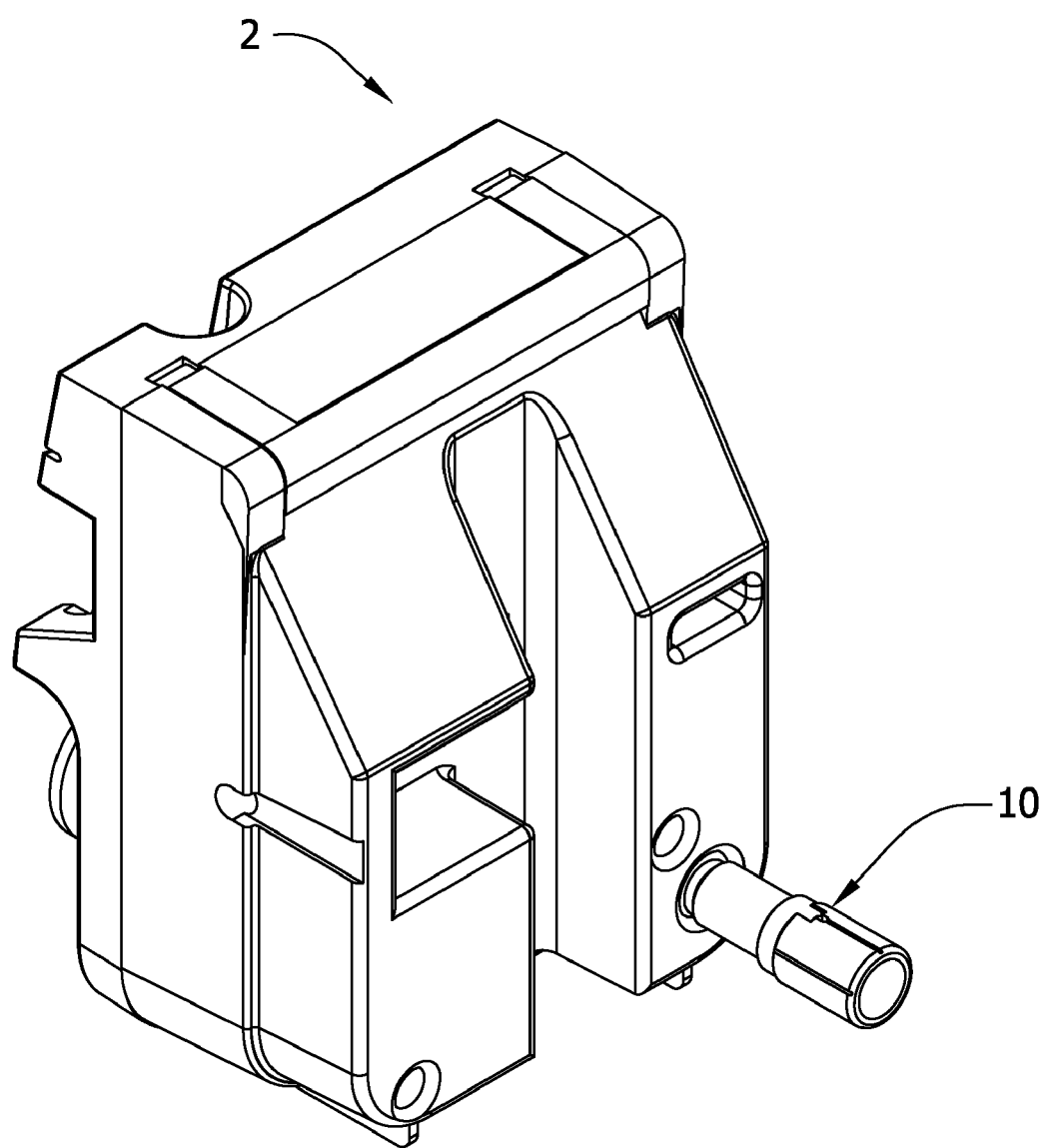
FIG. 21 is a perspective of a compression therapy device controller with an enlarged view of the connector.
Figure 22:
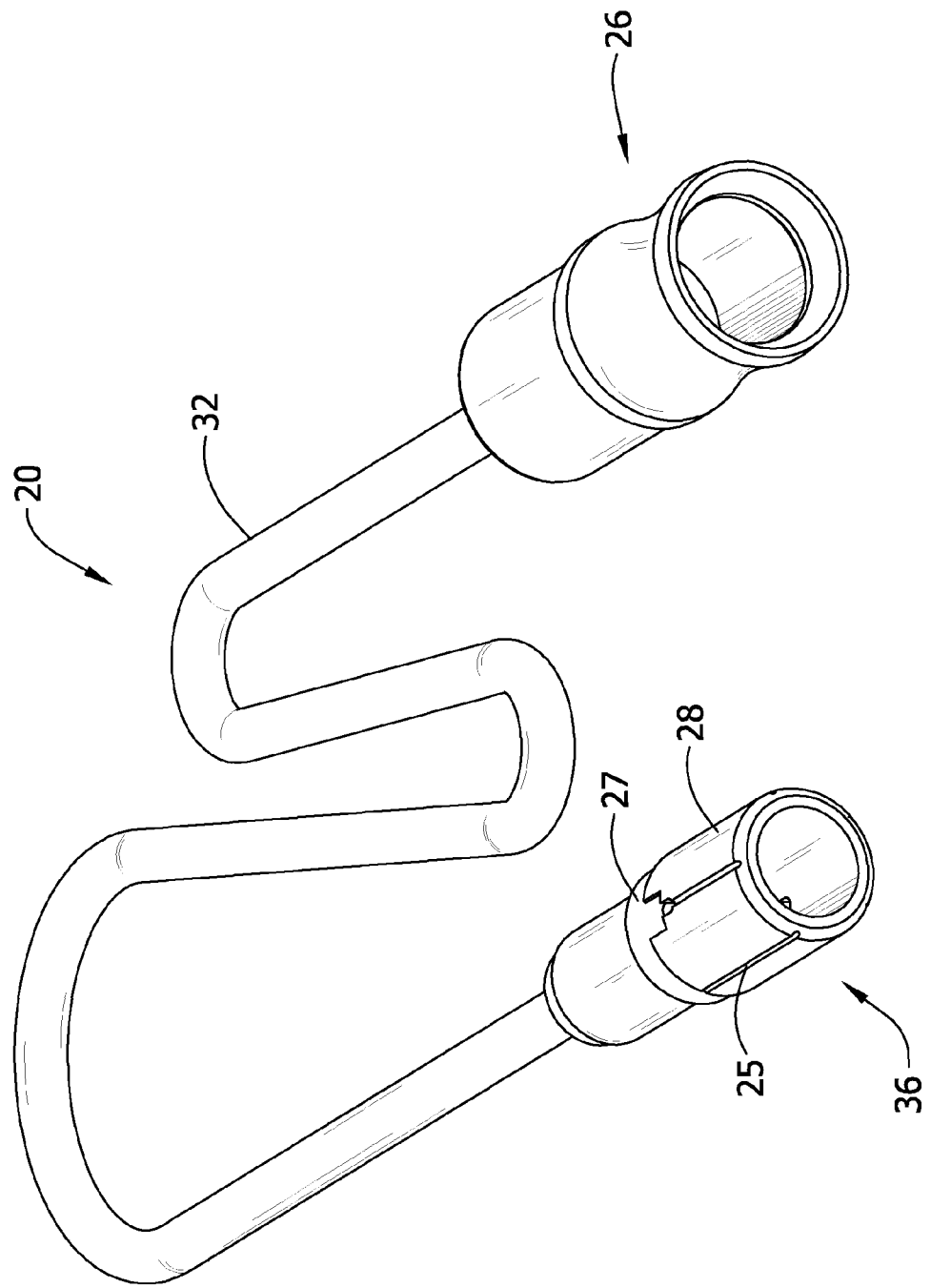
FIG. 22 is an enlarged perspective of a tube set.

In the illustrated example, a tube set 20 (FIG. 22) is used to selectively interconnect the compression therapy device 1 and the controller 2. The first connector 36 is attached to a first tubing 32 of the tube set 20, and the second connector 38 is attached to a second tubing 34 extending from the bladder 4 of the compression therapy device 1 (FIG. 20). A third connector 10 having substantially the same construction as the first connector 36 is attached to the controller 2 (FIG. 21), and a fourth connector 26 having substantially the same construction as the second connector 38 is attached to the opposite end of the tubing 32 of the tube set 20 (FIG. 22). In order to make fluid connection for delivering of pressurized air from the controller 2 to the compression therapy device 1, the fourth connector 26 of the tube set 20 is engaged with the third connector 10 of the controller, and the first connector 36 of the tube set is engaged with the second connector 38 of the compression therapy device. Because of the structural identity of the first connector 36 and third connector 10, and of the second connector 38 and the fourth connector 26, only the first and second connectors will be described in detail hereinafter.

Referring to FIGS. 1-6, the first connector 36 has an attachment portion 40 that accepts the tubing 32. However, the attachment portion 40 could be directly connected to an object other than tubing, such as the third connector 10 is directly connected to the controller 2 (FIG. 21). The second connector 38 has an attachment portion 80 and a receptacle 78. The receptacle 78 has a roughly hourglass shape, so the user can grasp and hold the connector apparatus 30 and to aid the user in engaging the second connector 38 to the first connector 36, as shown in FIG. 1.

Referring to FIG. 2, a coupling portion 42 of the first connector 36 has a first end 44 and a second end 46. The second end 46 is suitably attached to the attachment portion 40, such as by solvent bending or RF welding, or may be formed as one piece of material with the attachment portion. The attachment portion 40 is sealingly received in the tubing 32 of the tube set 20 (FIG. 22). The coupling portion 42 includes a sealing surface 48 and a non-sealing surface 52. The sealing surface 48 extends around the perimeter of the coupling portion 42 at the second end 46. The shape and contour of the coupling portion 42 is not restricted to that of the illustrated embodiment, so long as the coupling portion can engage and form a seal with the second connector 38, as will be described. The non-sealing surface 52 has a greater diameter than the sealing surface 48. A number of circumferentially spaced channels 58 in the non-sealing surface 52 extend lengthwise of the first connection 36. Two of the channels 58 communicate with openings 60 extending radially through the fist connector 36 to an inner surface 54 thereof. The channels 58 and openings 60 operate to inhibit the formation of a sealing connection.

Figure 3:
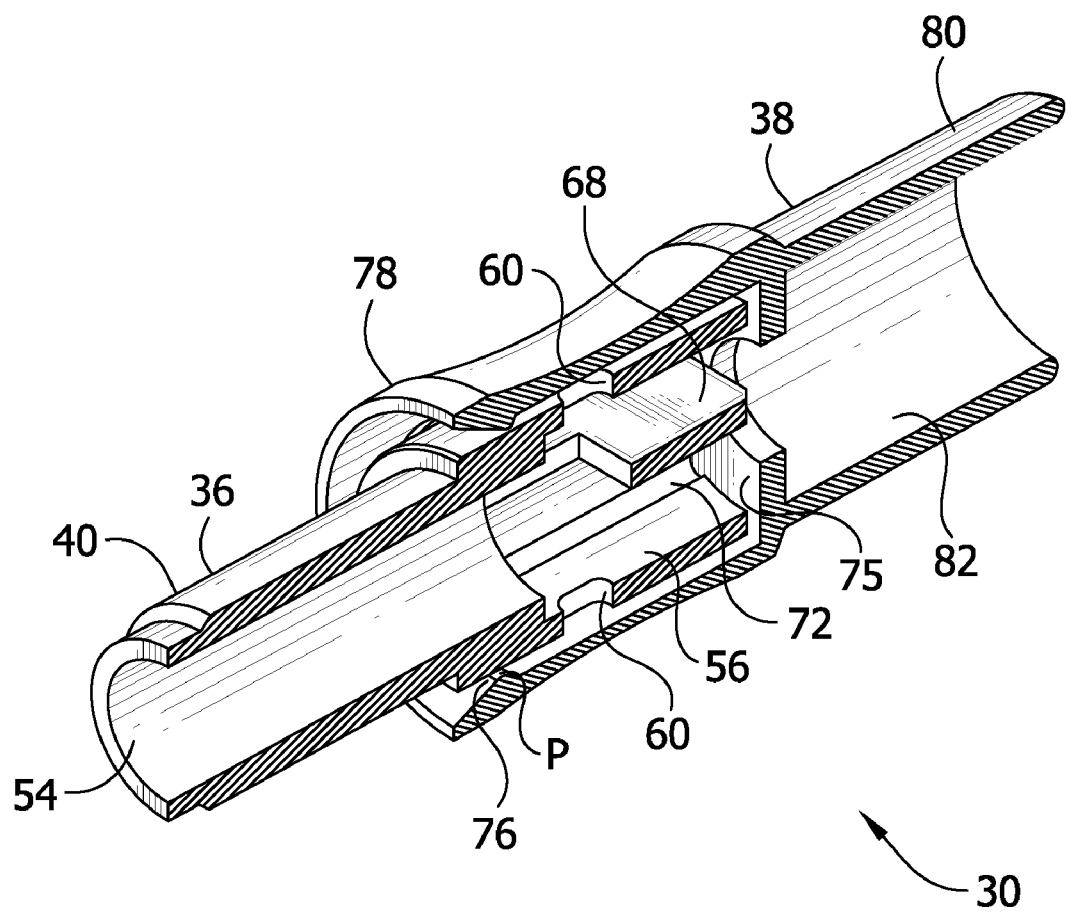
FIG. 3 is a perspective longitudinal section of the connector apparatus shown in FIG. 1.

The receptacle 78 of the second connector 38 has an interior surface 74 and an annular shoulder 75 at the inner end of the interior of the receptacle (FIG. 3). The shoulder 75 defines a stop surface that limits the distance the first connector 36 can be inserted into the receptacle 78 and axially positions the first connector 36 with respect to the receptacle 78. An annular sealing flange 76 projects radically inward of the inner surface 74 of the receptacle 78 near the open end of the receptacle. As illustrated, the sealing flange 76 is formed as one piece of material with the receptacle 78. However, a sealing member (not shown) may be formed separately from the receptacle (e.g., as an O-ring) and secured to the receptacle such as by being received in a circumferential groove formed in the inner surface of the receptacle.

The user must push, in the direction of the arrow "A" in FIG. 2, the first end 44 of the first connector 36 into the receptacle 78 of the second connector 38, such that the non-sealing surface 52 passes beyond the sealing flange 76. Unless the user pushes the connectors 36, 38 together, a fluid tight seal will not form because of longitudinal channels 58 disposed about the outer surface of coupling portion 42. The sealing flange 76 cannot conform into the channels 58 that extend past the flange allowing fluid to pass the flange on the non-sealing surface 52 of the first connector 36. However, when the sealing surface 48 moves into registration with the sealing flange 76, the flange is able to sealingly conform to the sealing surface to make a fluid tight connection with the sealing surface.

The open space defined by the longitudinal channels 58 prevents flush engagement of coupling portion 42 with the surface of a non-compliant connector or fluid conduit (lumen). The longitudinal channels 58 may have widths, depths, or lengths other than illustrated herein. One or more longitudinal channels 58 may be oriented parallel, offset, or undulating with the longitudinal axis of the connector 30. The longitudinal channels 58 can be replaced with a raised surface or roughness on the non-sealing surface 52. In addition, the openings 60 defined through a wall 62 help prevent a fluid seal between the first connector 36 and a non-compliant connector. An opening 60 is not limited to size and shape provided the opening leaks with a non-compliant connector attached to the first connector 36. One or more openings 60 diametrically opposed about the wall 62 facilitate leakage with a non-compliant connector.

Figure 2A:
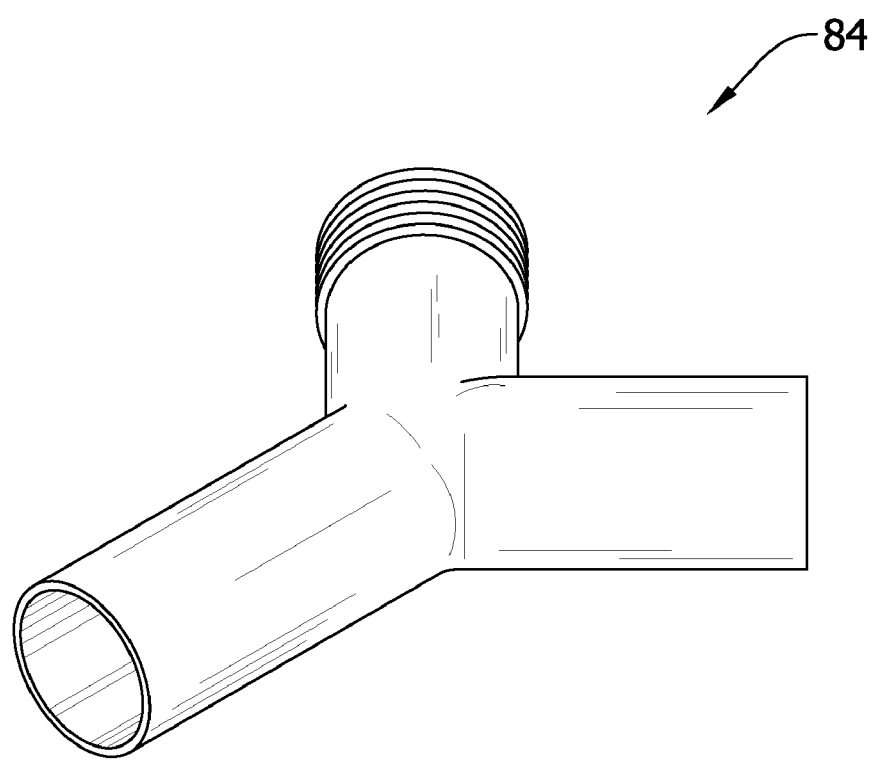
FIG. 2A is a perspective of a "Y" connector releasably attachable to the first or second connector.

An inner surface 54 of the first connector 36 and inner surface 74 of the second connector 38 form a fluid pathway therethrough. The inner surfaces (54, 74) are formed to pass fluid according to the particular flow requirements of a medical system such as the controller 2 and compression therapy device 1. Attachment portion 40 or attachment portion 80 is not restricted to one port. A "Y" connector 84 (FIG. 2A) is releasably attachable to the attachment portion (40, 80) of either connector 36,38 to increase the number of fluids or divert pressurized air to more than one bladder, in the case of compression sleeve.

FIG. 3 illustrates the connector apparatus engaged, without the tubing 32, 34 attached. In use, the first tubing 32 (not shown in FIG. 3) is sealingly attached to an inner surface 82 of the attachment portion 80. The second tubing (not shown in FIG. 3) is attached to attachment portion 40. The point contact "P" seals the connector apparatus 30 upon contact between the sealing flange 76 and the sealing surface 48 of the first connector 36. The tubing 32, 34 is attached in a suitable manner such as by using solvent bonding, RF welding, or other attaching means known in the art.

Figure 4:
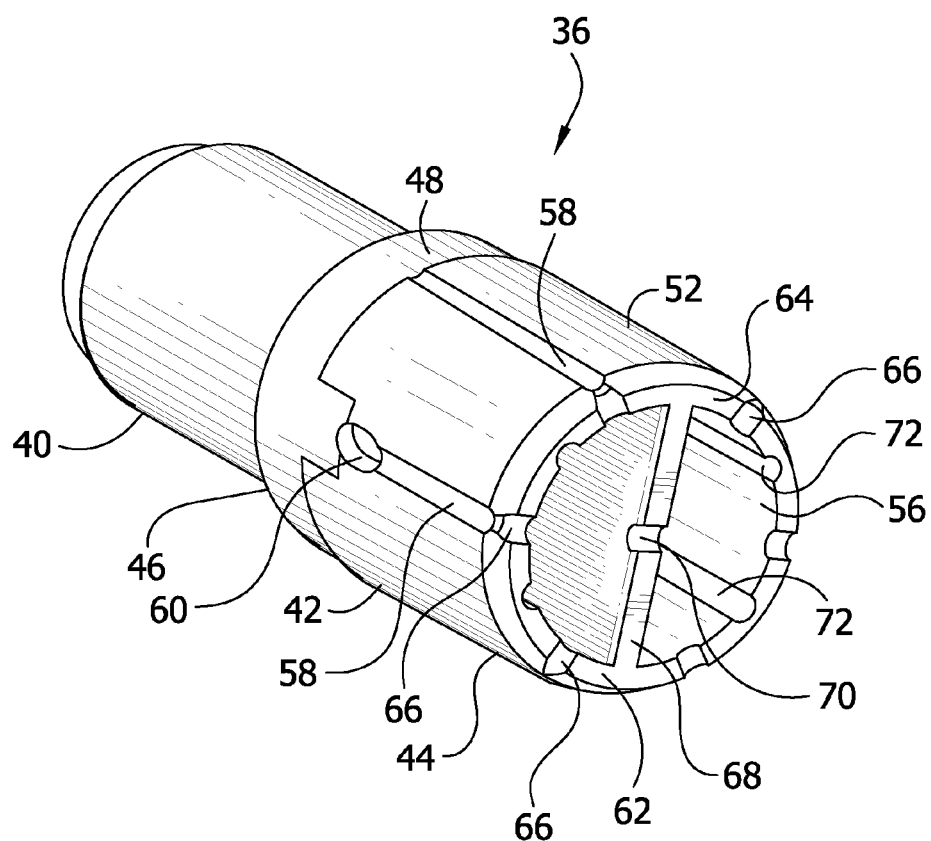
FIG. 4 is a perspective of the first connector of the connector apparatus shown in FIG. 1 seen from an end and to a side.
Figure 5:
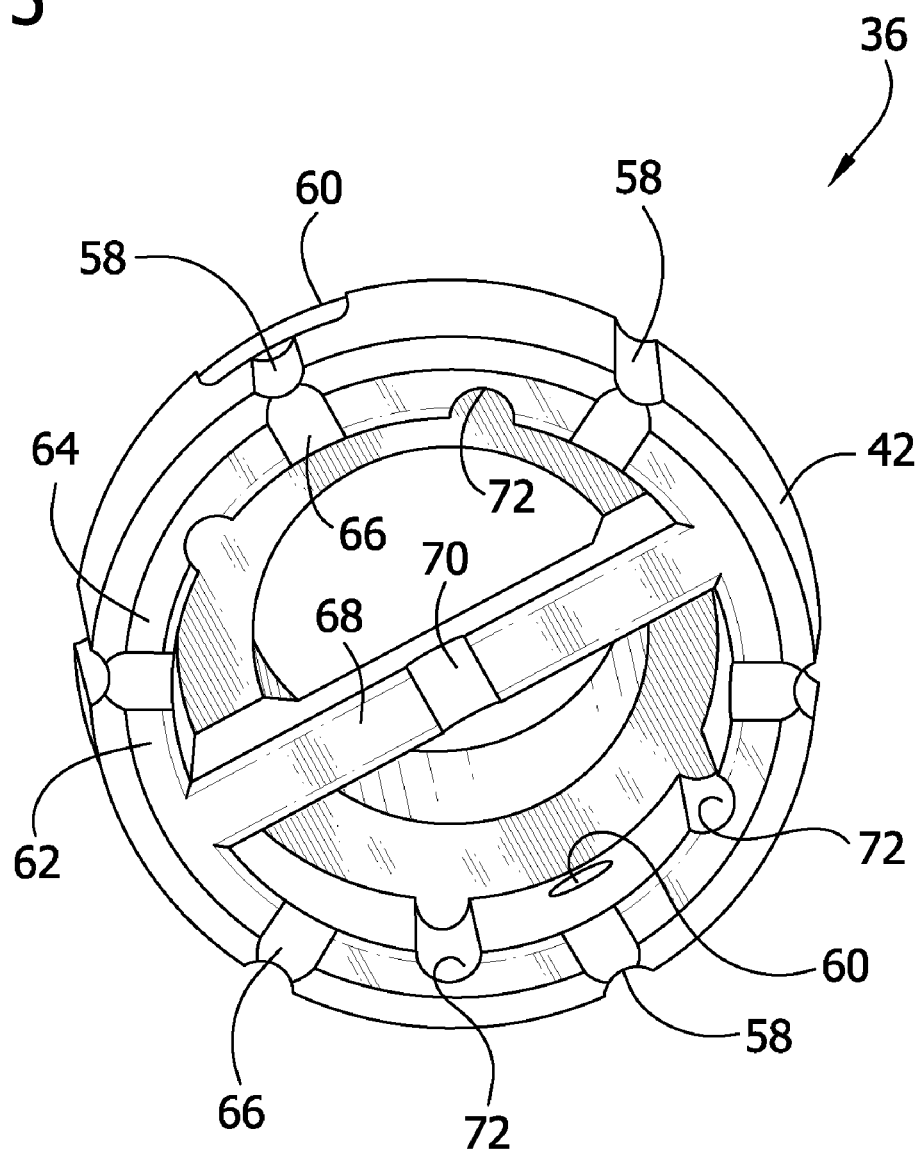
FIG. 5 is a perspective of the first connector seen substantially from the end.
Figure 6:
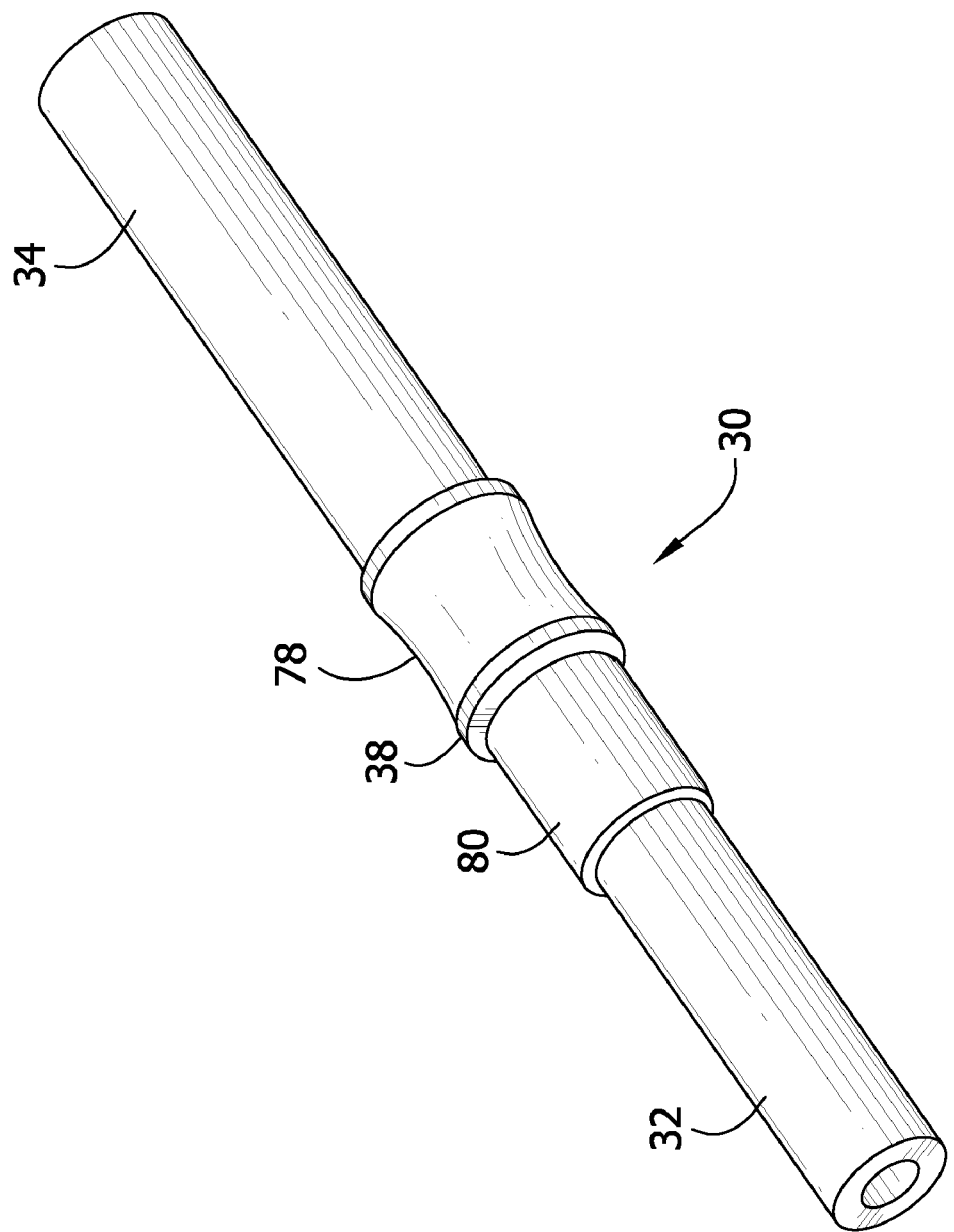
FIG. 6 is a perspective of the connector apparatus shown in FIG. 1 having tubing attached.

FIGS. 4 and 5 show a transverse wall 68 at the first end 44 of the first connector 36. The transverse wall 68 has a longitudinal cavity 70 across its face. The transverse wall 68 extends along the longitudinal axis for substantially the length of the non-sealing surface 52 and inhibits the insertion of tubes or other connectors (not shown) into the first connector 36. One or more longitudinal cavities 72 extend along the inner surface 56 at the first end 44. The non-sealing surface 52 has a first face 64 with transverse cavities 66 disposed at spaced locations around the perimeter of the first face 64. Each transverse cavity 66 connects to a corresponding one of the longitudinal channels 58 formed in the wall 62 of the coupling portion 42 of first connector 36. This allows fluid to escape between the first connector 36 and a non-compliant connector. Likewise, the openings 60 allow fluid to escape when a seal is not formed with the sealing surface 48. The number and arrangement of channels 58, openings 60 and cavities 66 may be other than described without departing from the scope of the present invention.

The cavities 66 prevent a seal between the first face 64 and a surface of a non-compliant connector. Each cavity 66 aligns with its corresponding outer longitudinal channels 58 to provide a path for leakage when the first connector 36 is inserted into a non-compliant connector. The transverse wall 68 prevents inserting a non-compliant connector into the first connector 36. The cavity 70 helps prevent a sealing surface between the first face 64 and a surface of a non-complaint connector. Likewise, inner longitudinal cavities 72 and the openings 60 though the wall 62 help prevent sealing with a non-compliant connector on the inside or outside of the first connector 36. The open spaces defined by the cavities 66 prevent flush engagement with coupling portion 42 and a surface of a non-compliant connector. A cavity or channel (66, 70, 72, 58) is not limited to a specific width, depth, or length. A cavity or channel (66, 70, 72, 58) is not restricted to orientation and can be parallel, offset or undulating. The present invention is not restricted to one non-sealing surface 52 or one sealing surface 48.

Figure 7:
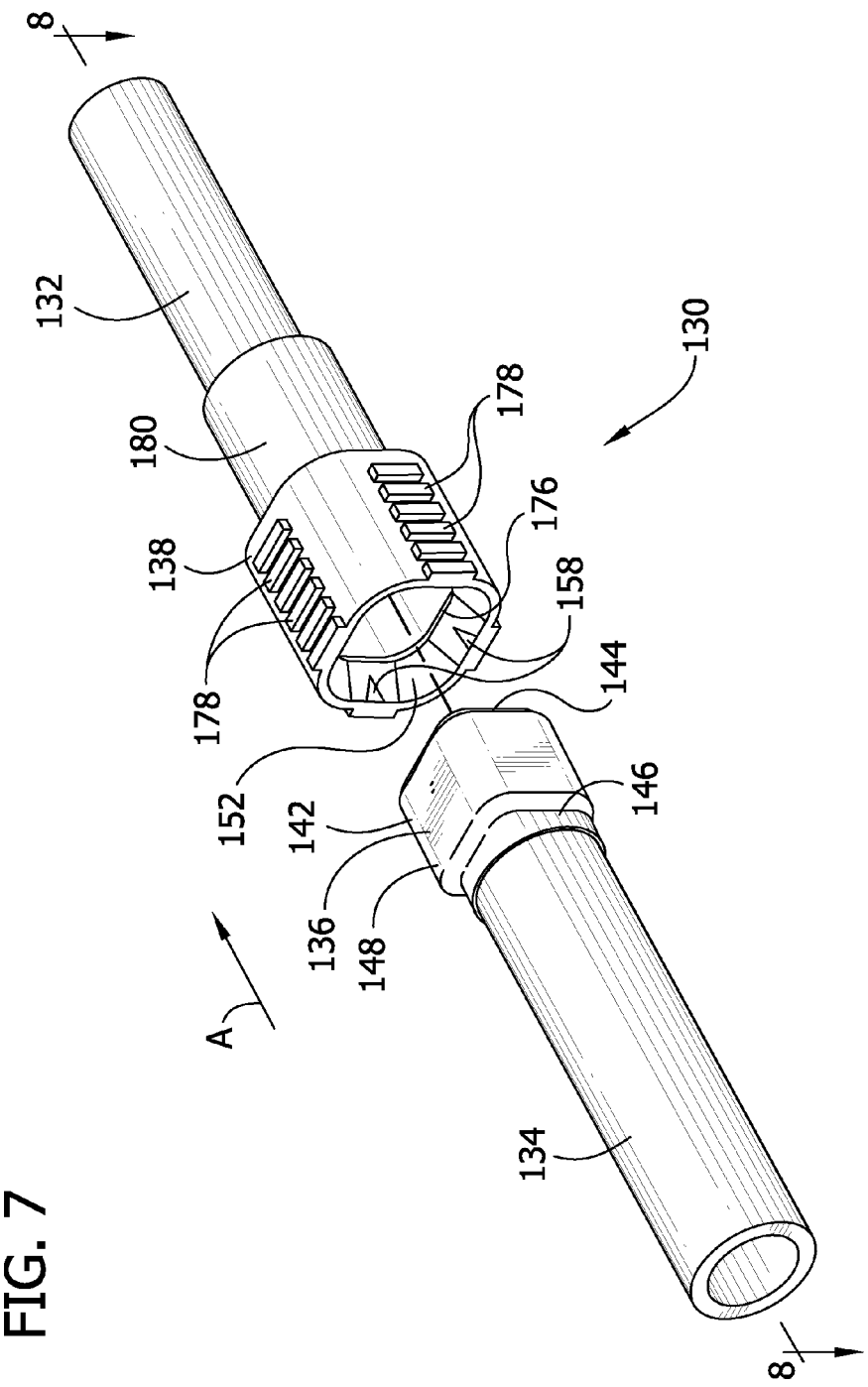
FIG. 7 is a perspective of an alternate embodiment of the connector apparatus showing two separated connectors with tubing attached.
Figure 8:
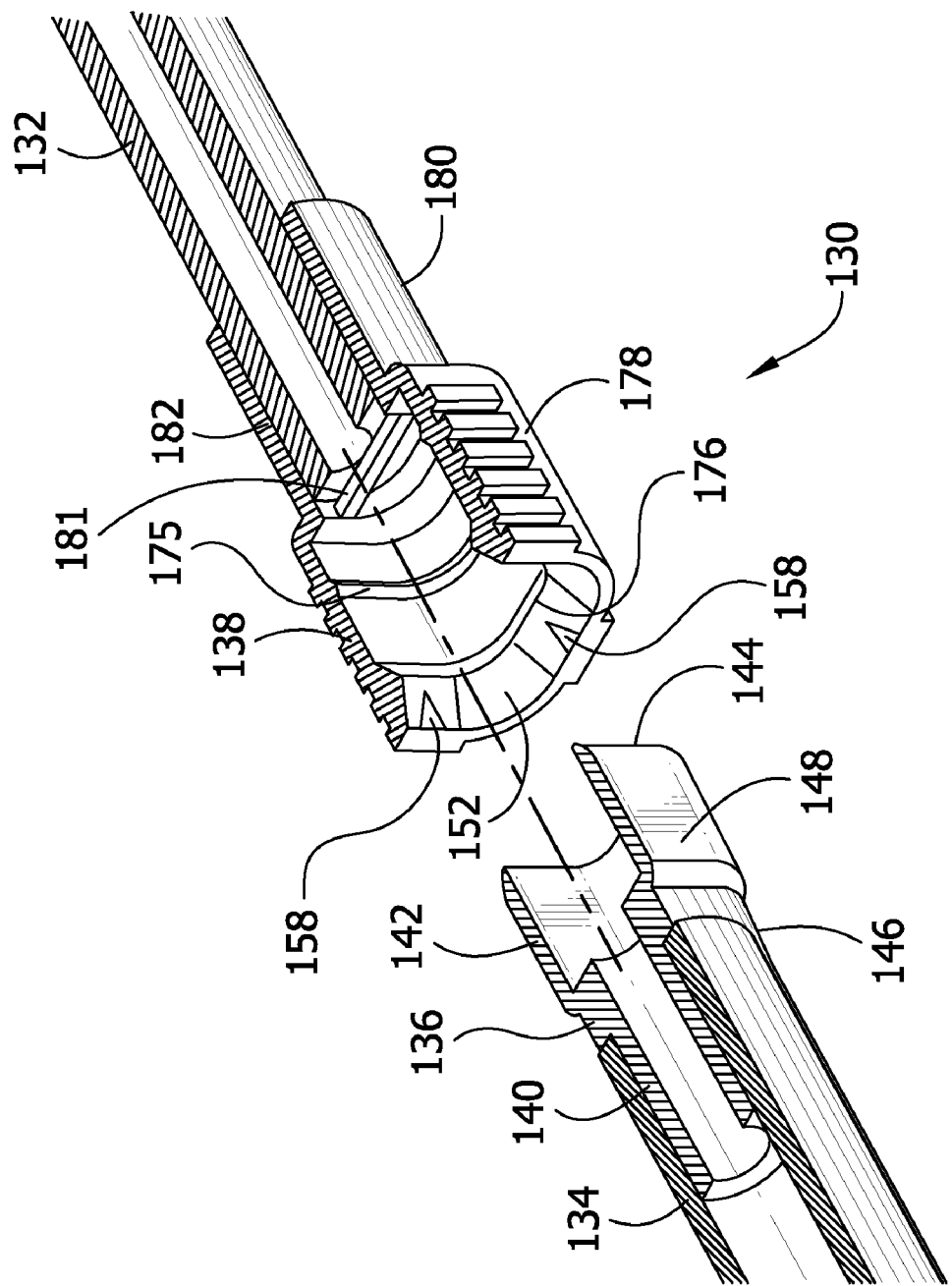
FIG. 8 is a perspective longitudinal section of the connector apparatus shown in FIG. 7.

FIGS. 7 and 8 illustrate an alternative connector apparatus 130. Parts of the connector apparatus 130 generally corresponding to those of the connector apparatus 30 will be given the same number, plus "100." A first connector 136 of the connector apparatus 130 has a first end 144 and a second end 146. Located generally between the first and second ends 144, 146 is a sealing surface 148. The coupling portion 142 is rectangular with rounded corners and sized to fit into the opening of a second connector 138, in the direction of arrow "A". The second connector 138 defines a receptacle in a housing of the second connector to receive the first connector 136. An outwardly flared non-sealing surface 152 is located at the open end of the second connector 138. Triangular channels 158 in the non-sealing surface provide fluid communication paths to locations outside the connectors 136, 138 to inhibit sealing.

The user holds the second connector 138 using raised ribs 178 to grip and insert the first connector 136 into the second connector 138. In addition to functioning as grips, the ribs 178 also prevent a sealing connection between the second connector 138 and a tube or the like (not shown) received over the exterior of the second connector. The first connector 136 is inserted with its first end 144 passing beyond a sealing flange 176 located inside the second connector 138. The resilient sealing flange 176 conforms to the sealing surface 148 to form a fluid tight seal, after the sealing surface 148 passes beyond the non-sealing surface 152 and engages the flange 176. The user stops applying force when the face of the first end 144 abuts a shoulder 175 a distance beyond the sealing flange 176 of the second connector 138. A bar 181 is located at the inner end of the second connector 138 to inhibit a tube (not shown) from sealingly abutting a first tube 132 inserted inside an attachment portion 180 of the second connector.

The first tubing 132 forms a sealing interference fit with the inner surface 182 of the attachment portion 180. A second tubing 134 is inserted over an attachment portion 140 (FIG. 8), at the second end 146 of the coupling portion 142. The first and second tubings 132, 134 are attached in suitable ways to the first and second connectors 136, 138. This forms a fluid conduit as part of a medical system when properly connected.

Figure 9:
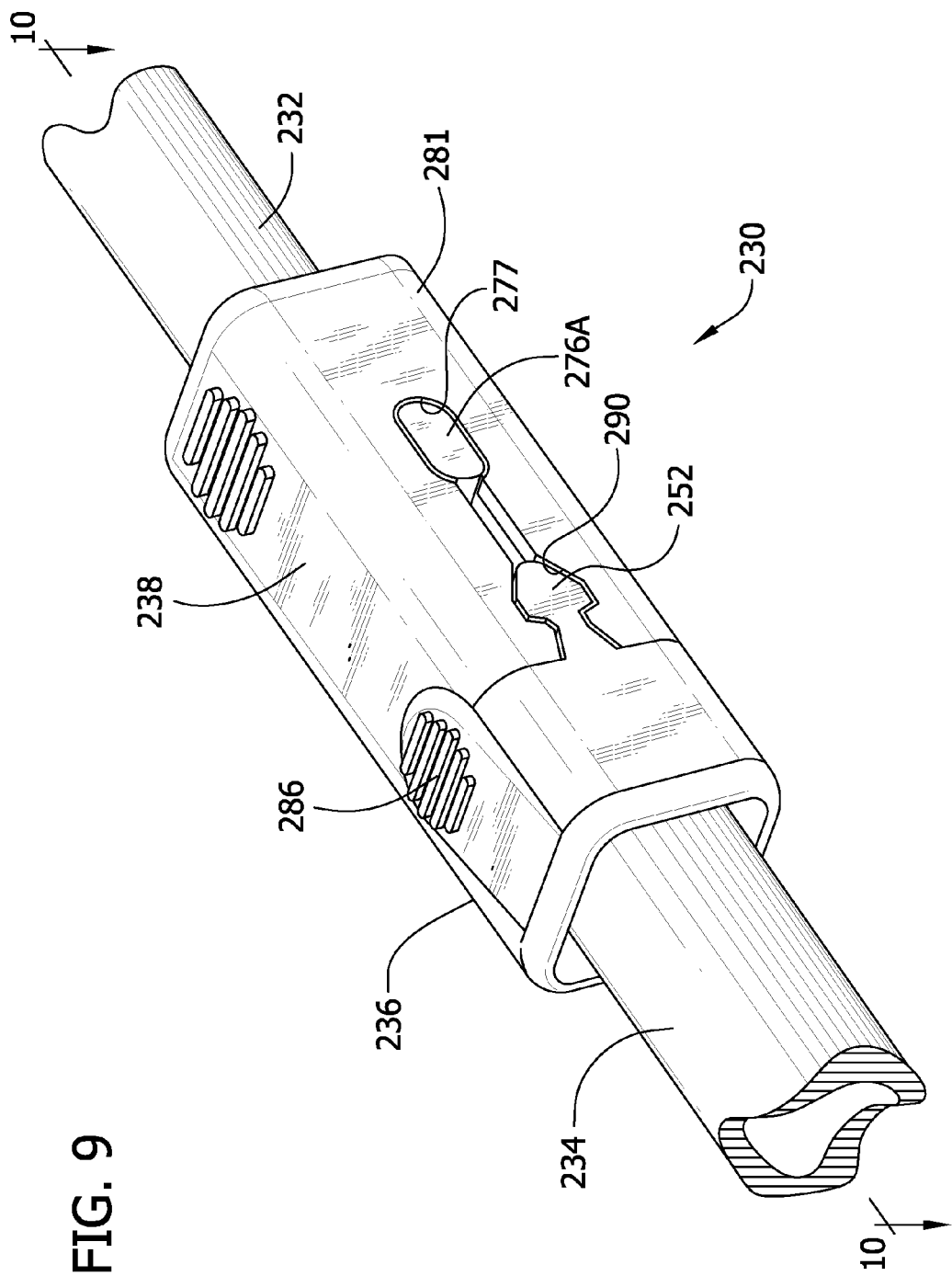
FIG. 9 is a perspective of another alternative embodiment of the connector apparatus with tubing attached.
Figure 10:
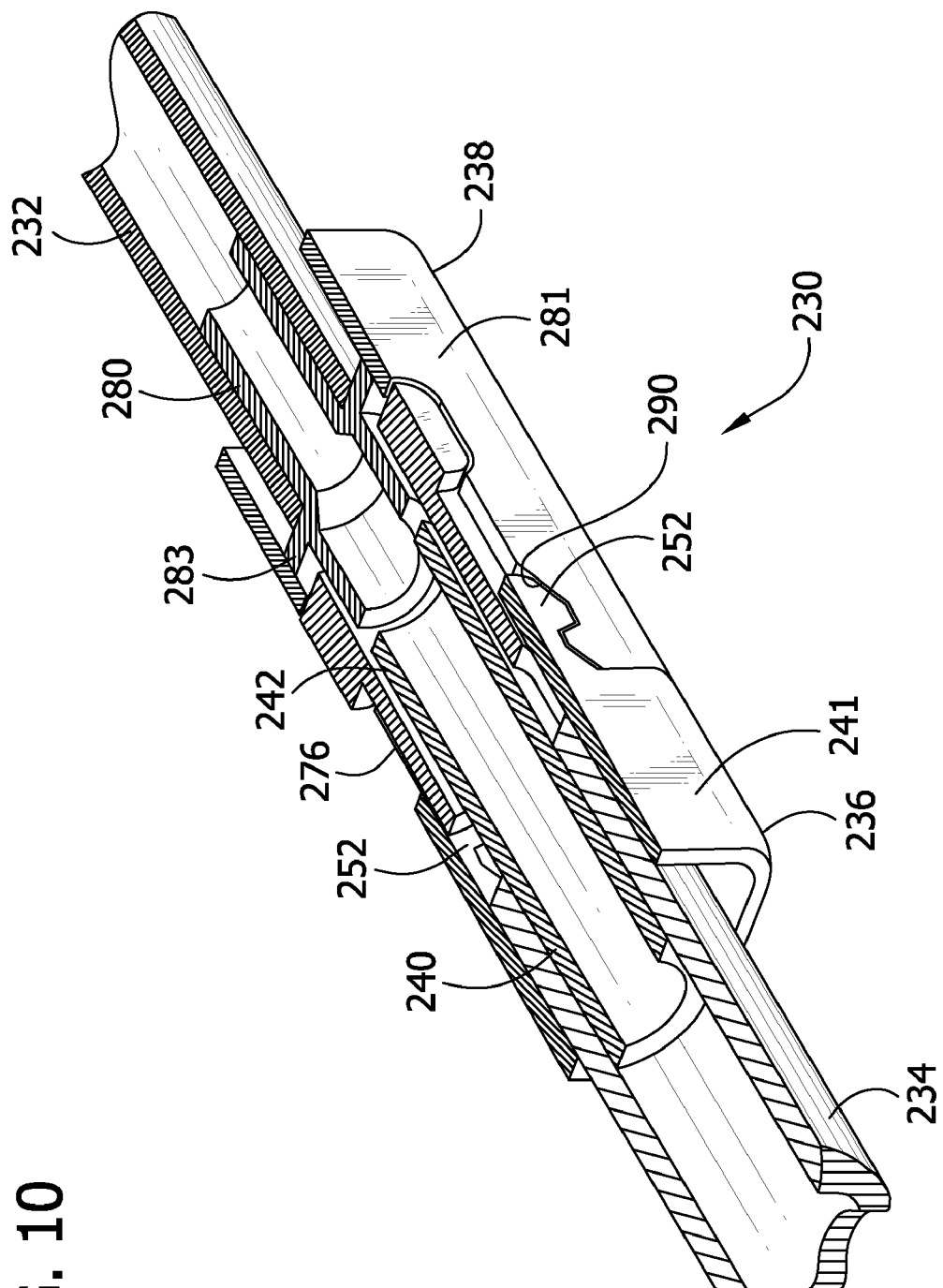
FIG. 10 is a perspective longitudinal section of the connector apparatus as shown in FIG. 9.
Figure 11:
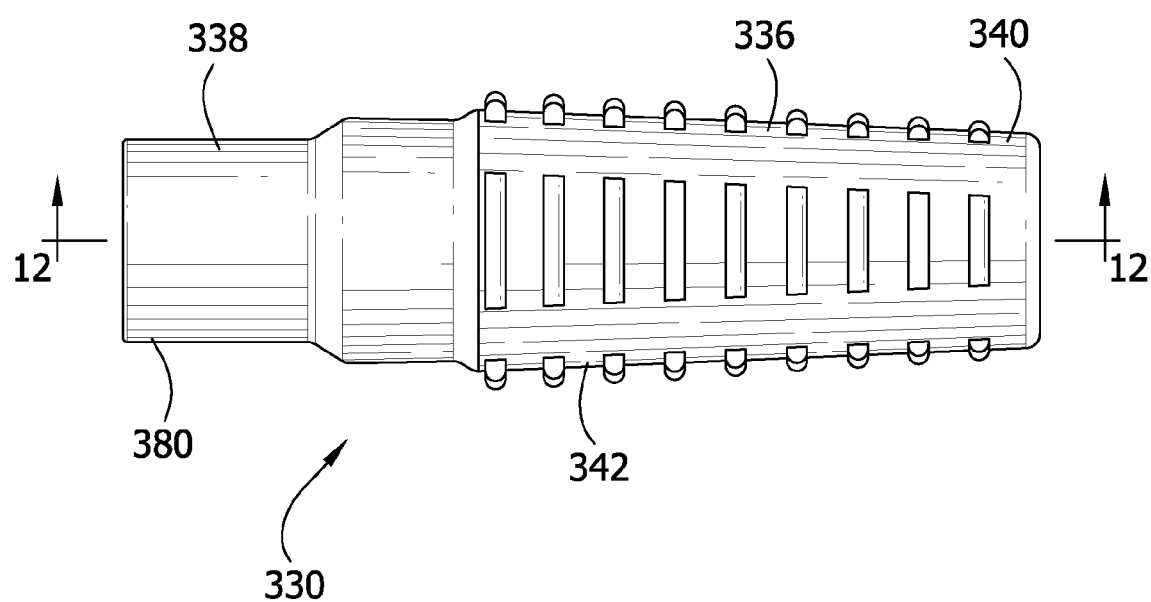
FIG. 11 is a side elevation of another alternative embodiment of the connector apparatus with the first and second connectors engaged.
Figure 12:
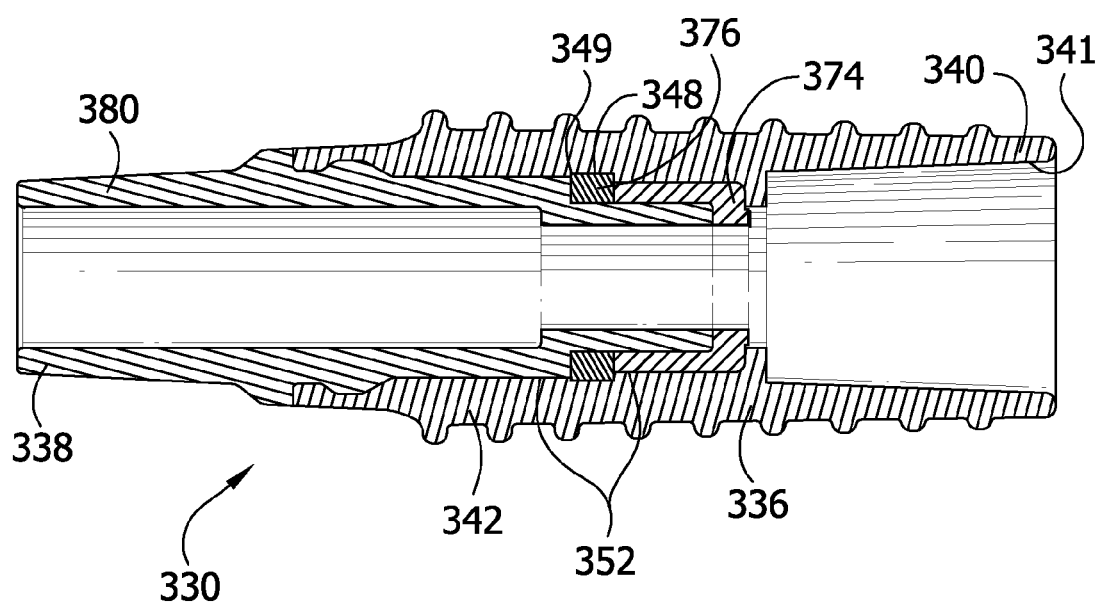
FIG. 12 is a longitudinal section of the connector apparatus shown in FIG. 11.

FIGS. 9 and 10 illustrate a connector apparatus 230 comprising a key 252 and a mating cavity 290. Parts of the connector apparatus 230 corresponding to those of the connector apparatus 30 are given the same reference numeral, plus "200." When the key 252 is positioned in the cavity 290, the user has established a fluid-tight seal within the connector apparatus 230. The connector apparatus 230 comprises a first connector 236 and a second connector 238. The first connector 236 has a tubular attachment portion 240 secured to an interior of a housing 241 of the first connector. The attachment portion 240 can be sealingly received in a (second) tubing 234. The second connector 238 has an attachment portion 280 that can attach the second connector to a (first) tubing 232. The second connector 238 includes a housing 281 that mounts the attachment portion 280 by way of a flange 283 of the attachment portion. A gasket 276 (broadly, "a sealing member") mounted by the housing 281 is generally tubular in shape and includes ears 276a that are received in correspondingly shaped openings 277 in the housing 281. The gasket 276 is received around and sealingly engages an exterior surface of the attachment portion 280 axially inward of the mounting flange 283.

Coupling portion 242 is slidingly and sealingly received by a first end of second connector 238 into the gasket 276 to form a sealing connection between the first and second connectors. The key 252 snaps into the mating cavity 290 to releasably lock the first and second connectors 236, 238 is sealing connection. To release the first connector 236, the user depresses a button 286, with raised edges, and pulls the first connector 236 from the second connector 238, while holding the second connector 238. Depressing the button 286 deforms the first connector and moves the key 252 laterally out of the cavity 290. The key 252 prevents engagement with a non-compliant connector (not shown).

Figure 19:
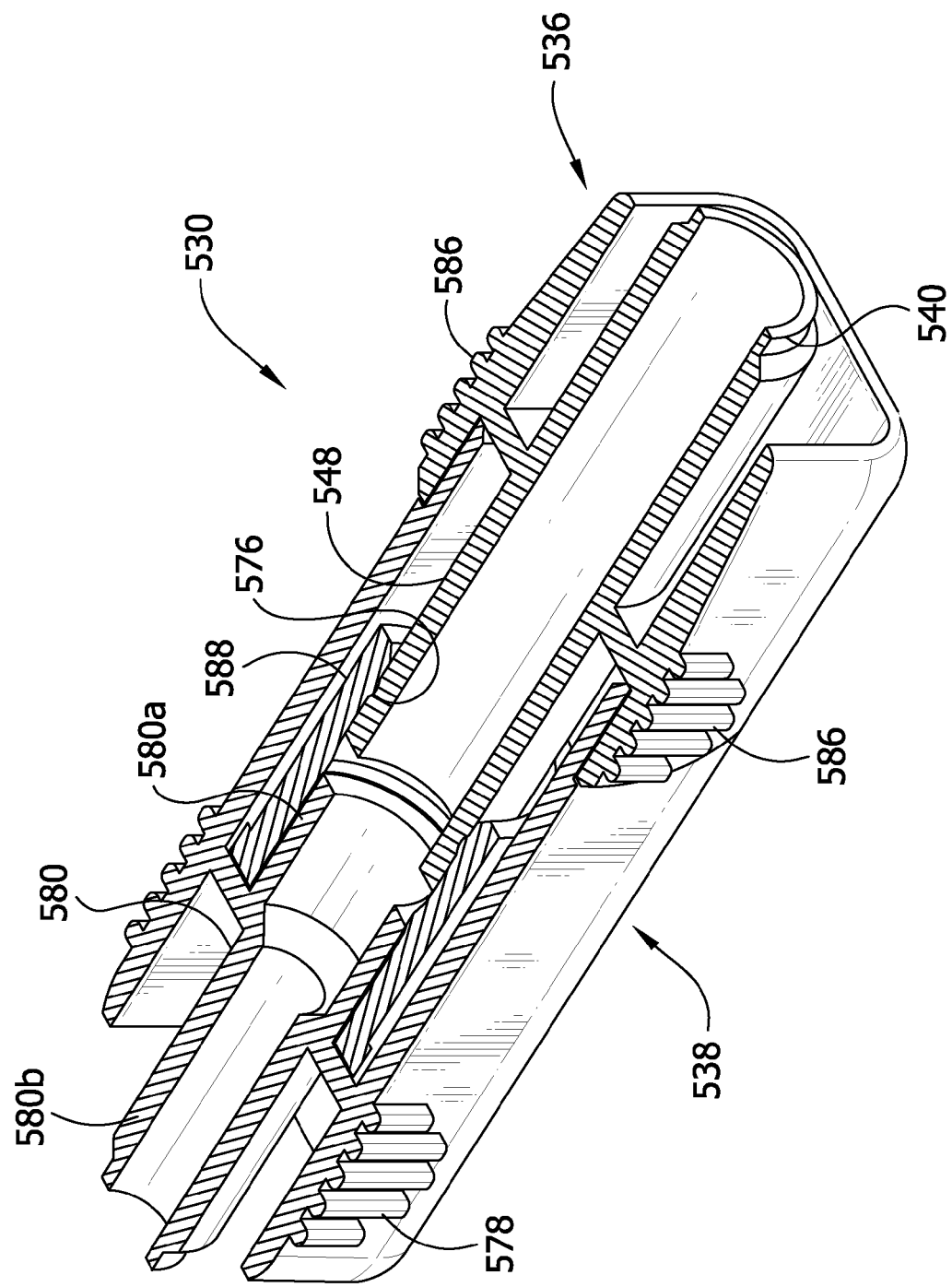
FIG. 19 is perspective longitudinal section of the engaged first and second connector of the connector apparatus shown in FIG. 9.
Figure 19A:
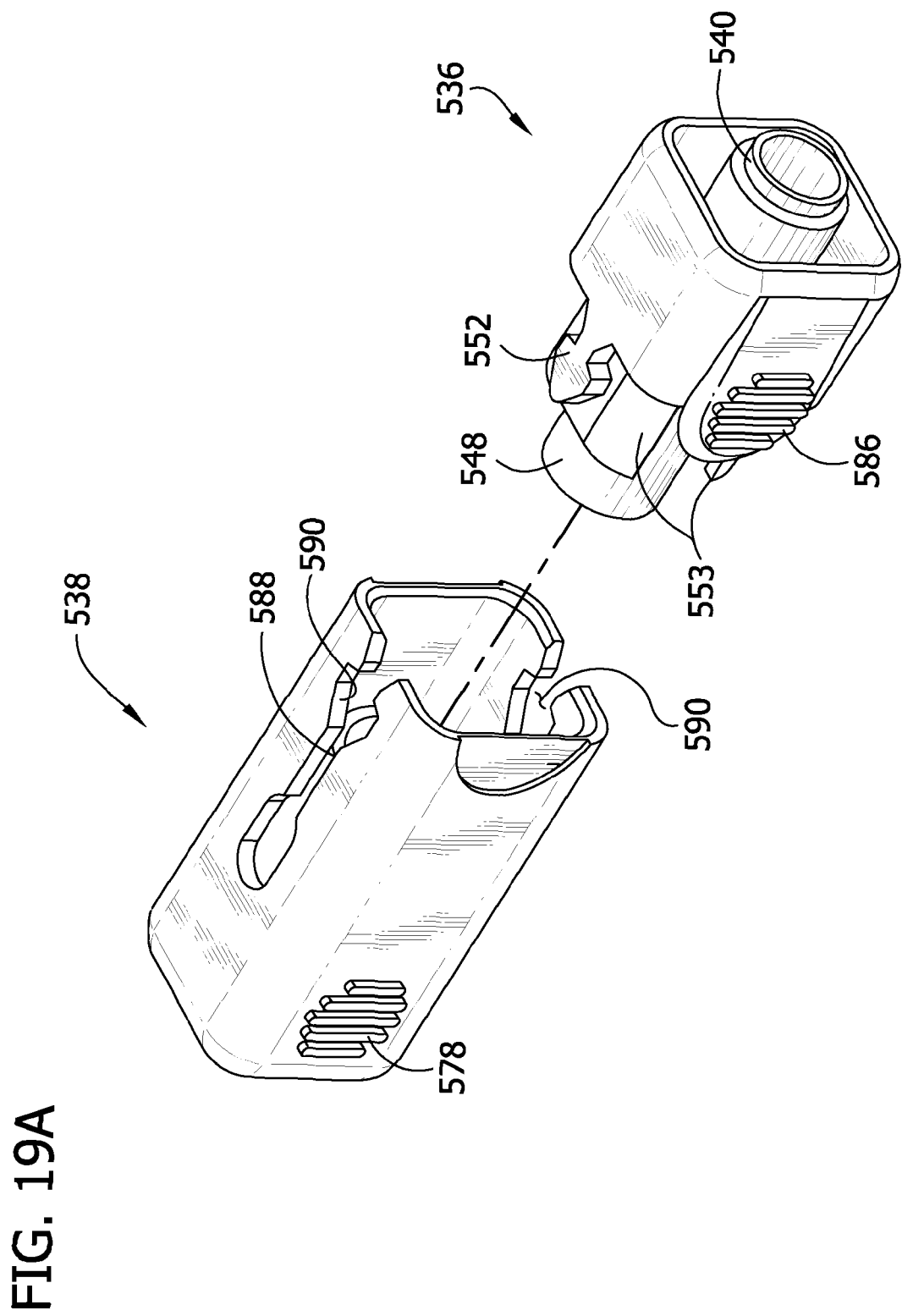
FIG. 19A is a perspective of the first and second connector separated of the connector apparatus shown in FIG. 9.

An alternate embodiment of a keyed connector apparatus 530 illustrated in FIGS. 19 and 19A is similar to the keyed connector apparatus 230 of FIGS. 9 and 10. Parts of the connector apparatus 530 corresponding to those of the connector apparatus 30 are given the same reference numeral, plus "500." The first connector 536 comprises a key 552, guide flanges 553 and an inner rigid lumen or conduit 548 including an attachment portion 540. The second connector 538 comprises a mating cavity 590, an inner sealing member 588, and finger grips 578 An attachment portion 580 located within the second connector 538 includes an inner part 580a that is sealingly attached to the sealing member 588, and an outer part 580b that can be attached to tubing (not shown). In operation, the user grips the second connector 538 at the finger grips 578, grips the first connector 536 and then pushes the key 552 toward the cavity 590 until it snaps into the cavity. The flanges 553 engage the second connector 538 and help guide the first connector 536 into sealing engagement with the second connector. The inner end of the conduit 548 is received in the sealing member 588 and seals with the sealing member by engagement with an annular protrusion 576 in the sealing member. In this way, a sealing connection of the first and second connectors 536, 538 can be made.

Figure 13:
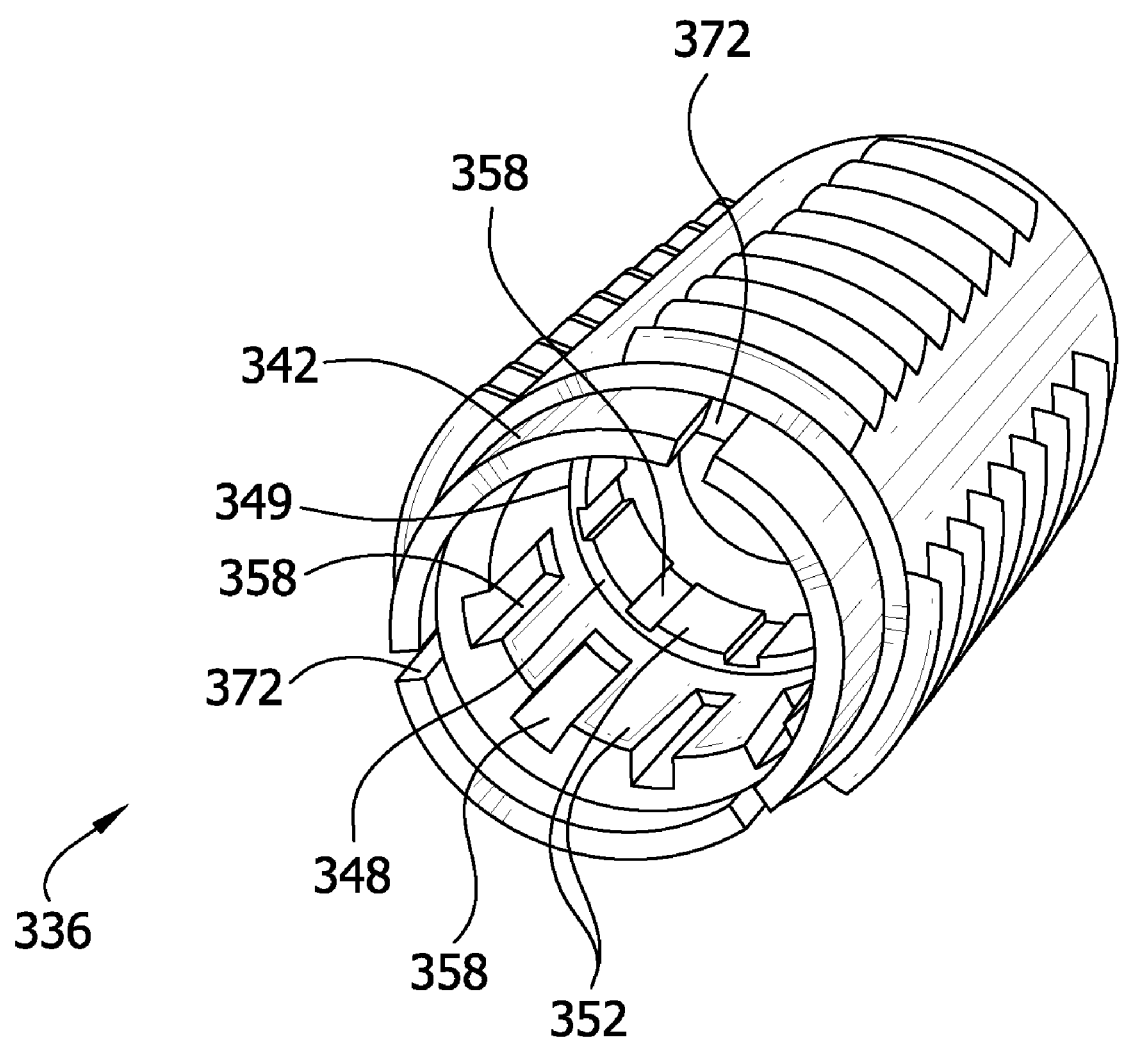
FIG. 13 is a perspective of the first connector of the connector apparatus shown in FIG. 11.
Figure 14:
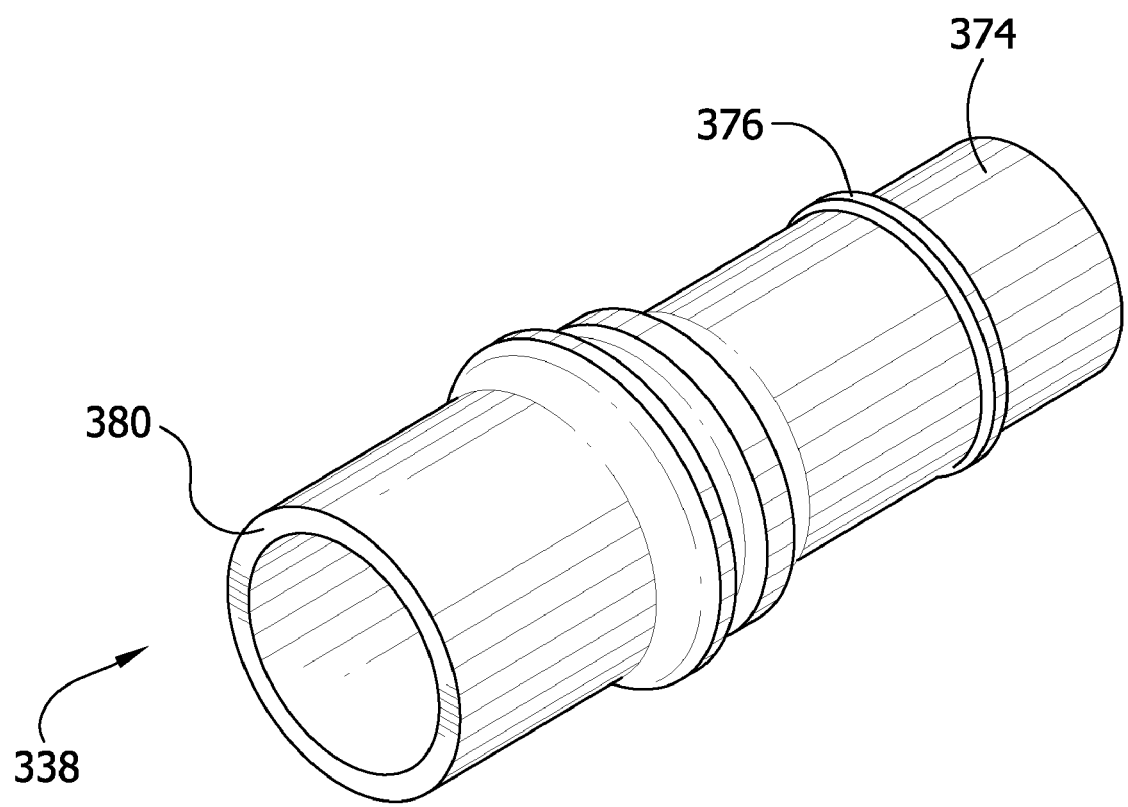
FIG. 14 is a perspective of the second connector of the connector apparatus shown in FIG. 11.
Figure 15:
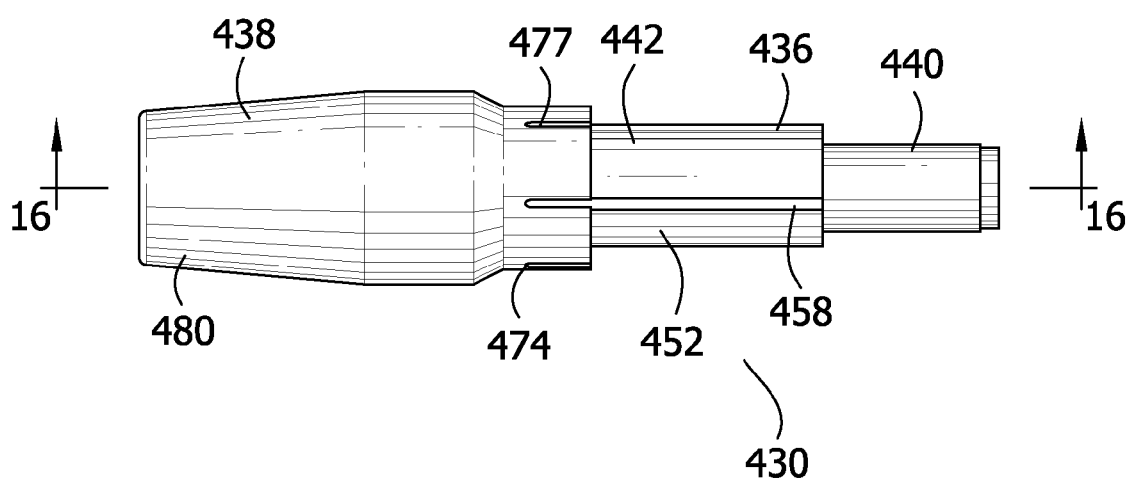
FIG. 15 is a side elevation of another alternative embodiment of the connector with the first and second connectors engaged.

FIGS. 11-14 illustrate still another alternate embodiment of a connector apparatus 330. Parts of the connector apparatus 330 corresponding to those of the connector apparatus 30 are designated by the same reference numerals, plus "300." Connector apparatus 330 comprises a first connector 336 (FIG. 13), and a second connector 338 (FIG. 14). First connector 336 has an attachment portion 340 (FIG. 12) that accepts tubing (not shown) on the inner surface 341 of the attachment portion 340. The second connector 338 (FIG. 14) has an attachment portion 380 at a first end and a cap 374 at the second end. A second tubing (not shown) can be received on attachment portion 380. Spaced a distance from the second end is a deformable O-ring 376 around the perimeter of the cap 374. The O-ring 376 is releasably attached to the cap 374. It will be understood that a sealing member can be formed in any suitable manner such as an O-ring (as shown) or a raised surface of deformable plastic.

The first connector 336 further comprises a coupling portion 342 with at least one longitudinal channel 372 therethrough (FIG. 13). A plurality of non-sealing surface 352 areas (FIGS. 12 and 13) are disposed on the inside of the coupling portion 342. The non-sealing surfaces 352 have longitudinal channels 358 disposed on the inner surface of the first connector 336 to prevent a fluid seal with a non-compliant connector. The axially inner longitudinal channels 358 are also disposed on both sides of a groove 349 that defines the sealing surface 348 (FIG. 13). At the face of the coupling 342 are disposed a plurality of longitudinal channels 372 (FIG.

13). The open space defined by the channels 372 prevents the coupling portion 342 from forming a fluid seal with a surface of a non-compliant connector.

In operation, the user inserts the cap 374 into the opening at the coupling portion 342. The O-ring 376 is deformed as it moves over the non-sealing surfaces 352 under the force of the user. The O-ring 376 comes to rest in the groove 349 and engages the sealing surface 348 (FIG. 13), to form a fluid tight seal.

FIGS. 15-18 illustrate a further embodiment of a connector apparatus 430. Parts of the connector apparatus 430 corresponding to those of the connector apparatus 30 are given the same reference numerals, plus "400." Connector apparatus 430 includes a first connector 436 and a second connector 438. The first connector 436 has an attachment portion 440 that can be attached to a lumen (not shown) which fluidly communicates with a fluid source. A lumen (or tubing) is received on an outer surface of attachment portion 440 and forms a fluid-tight seal therewith. The first connector 436 has a coupling portion 442 comprising a sealing surface 448 and a pair of non-sealing surfaces 452 and each non-sealing surface 452 having longitudinal channels 458 (FIG. 17) disposed on the inner and outer surfaces of the coupling portion 442. The longitudinal channels 458 are disposed on either side of the sealing surface 448. The longitudinal channels 458 prevent a sealing engagement with the coupling portion 442 by a non-compliant connector. A longitudinal channel 458 can be oriented anywhere along the perimeter of the coupling portion 442 and can be of varying length, width or depth. A generally annular detent 479 (broken by channels 458) extends around the first connector 436.

The non-sealing surface 452 includes a first face 464. The first face 464 includes a transverse wall 468 that extends across the diameter of coupling portion 442. Transverse wall 468 is configured to prevent sealing engagement of the surface of coupling portion 442 with a non-compliant connector.

Figure 16:
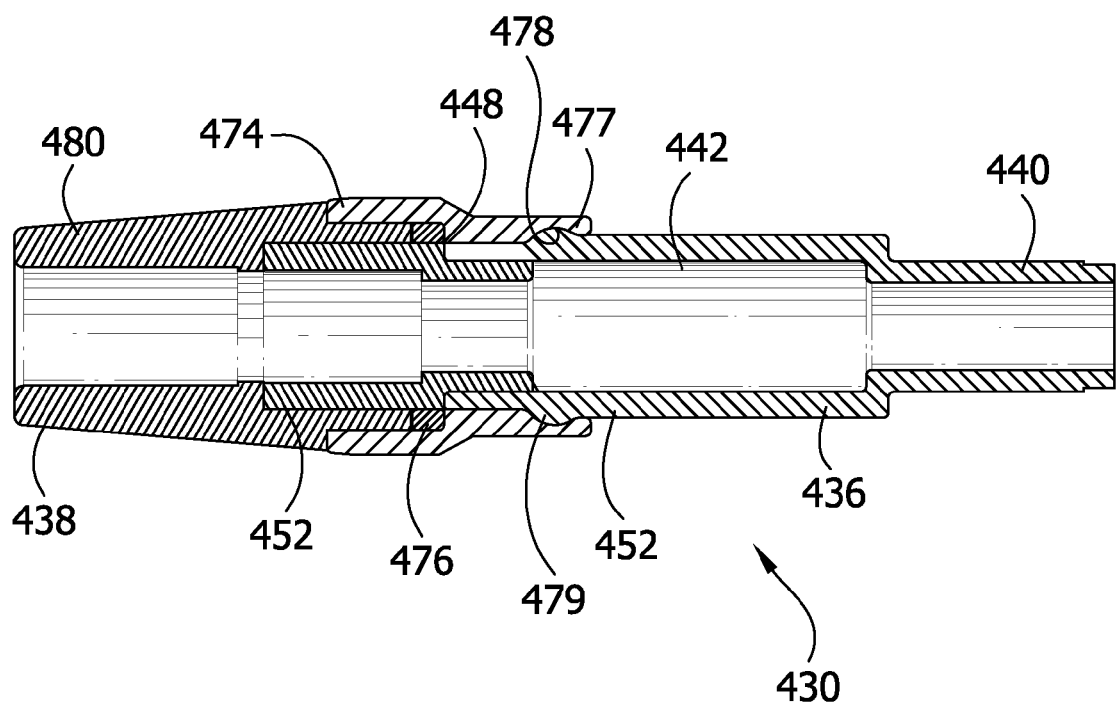
FIG. 16 is a longitudinal section of the connector apparatus shown in FIG. 15.
Figure 17:
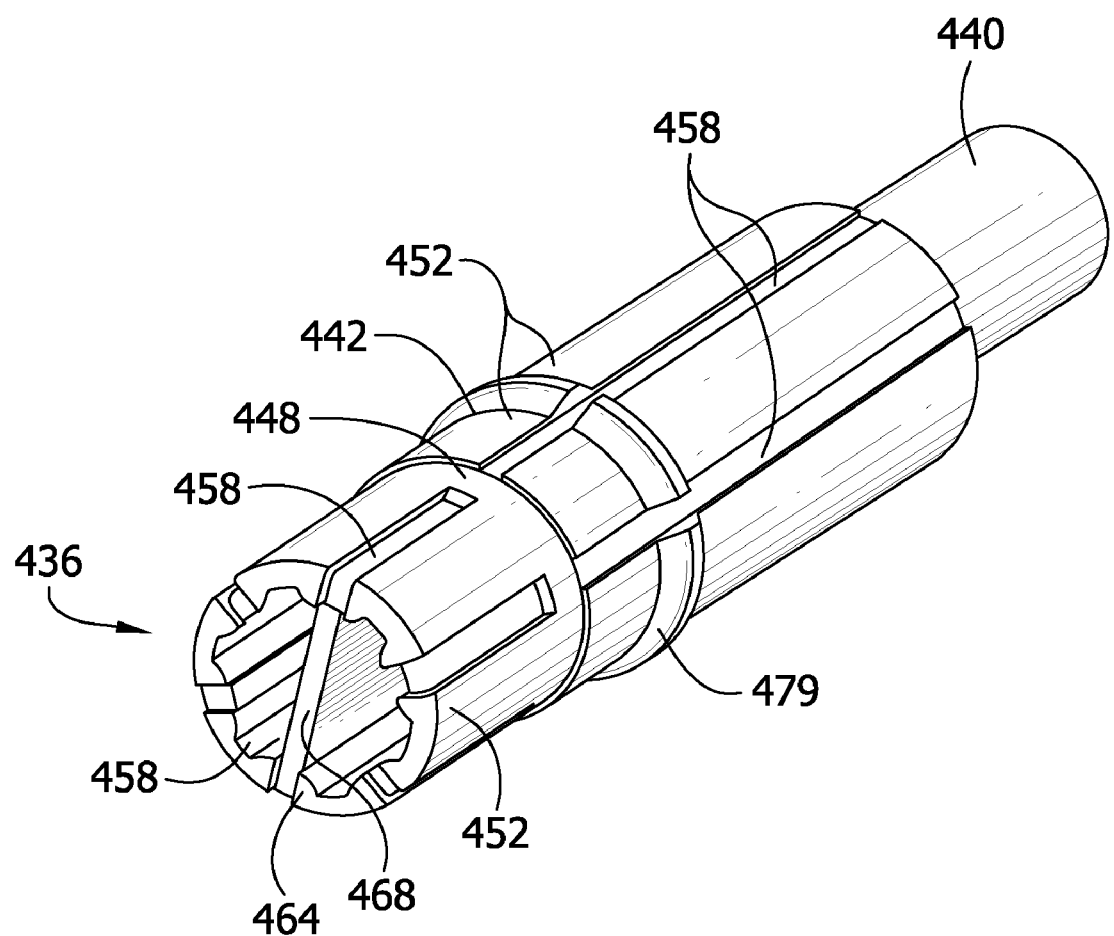
FIG. 17 is a perspective of the first connector of the connector apparatus shown in FIG. 15.
Figure 18:
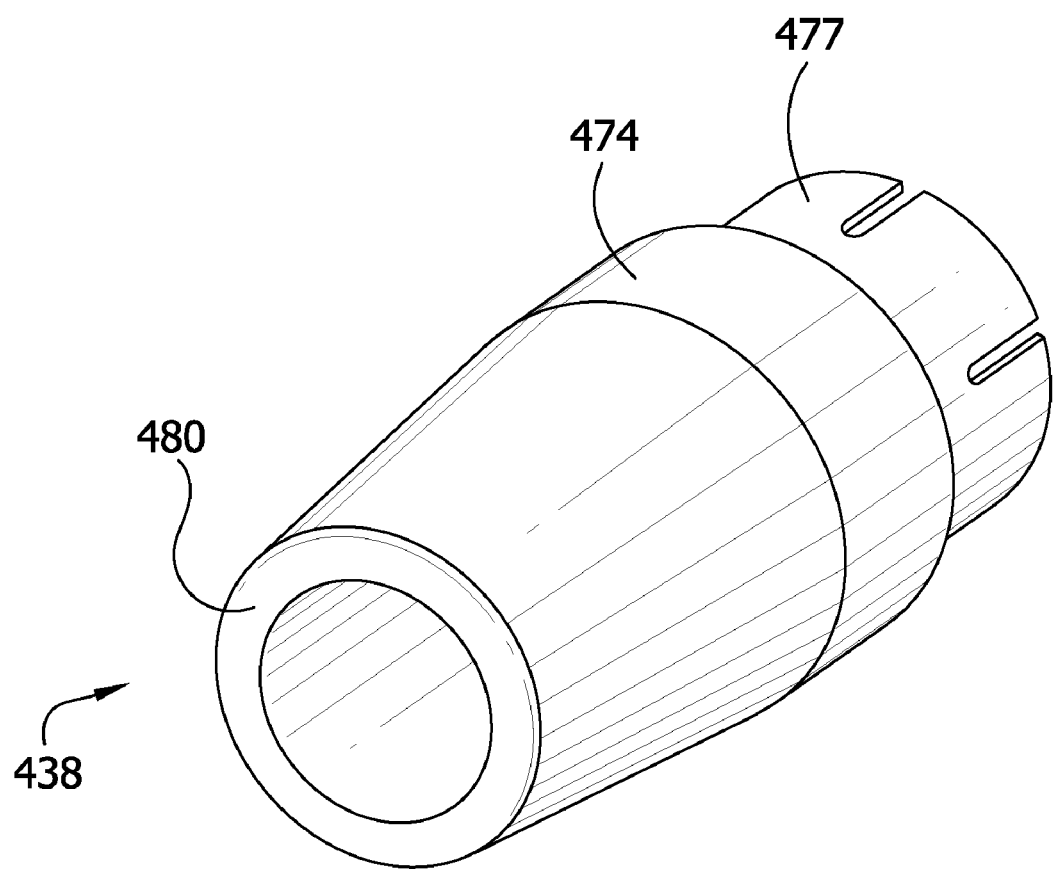
FIG. 18 is a perspective of the second connector of the connector apparatus shown in FIG. 15.

The second connector 438 comprises an attachment portion 480, a cap 474, an O-ring 476 inside the cap and sealingly mounted on the cap, and a flex collar 477 (FIGS. 16 and 18). In operation, the user pushes the second connector 438 onto the coupling portion 442, with the first face 464 entering the opening of the second connector 438, at the flex collar end. The O-ring 476 engages the leading non-sealing surface 452 and does not establish a sealing connection with the non-sealing surface because of the channels 458. The O-ring 476 next engages the sealing surface 448 as the first connector 436 is advanced farther into the second connector 438 and establishes a sealing connection between the first and second connectors. The detents 479 of the first connector 436 are received in annular grooves 478 on the interior of the flex collar 477. The flex collar, which has been deflected from its relaxed position, bears against the detents 479 and holds them in the grooves 478 for securing the first and second connectors 436, 438 together.

For the preferred embodiments described herein, the connectors are fabricated from semi-flexible and flexible materials suitable for vascular compression therapy such as, for example, polymeric materials, depending on the particular vascular therapy application and/or preference. Urethanes and silicones may also be used. One skilled in the art, however, will realize that other materials and fabrication methods suitable for assembly and manufacture, in accordance with the present disclosure, also would be appropriate. A number of alternating sealing and non-sealing surfaces is possible depending on the size and shape of the connector apparatus.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above embodiments and methods without departing from the scope of the invention, it is intended that all matter contained in the above description and shown in the accompanying drawings shall be interpreted as illustrative and not in a limiting sense.

What is claimed is:

1. A tube set for use in making discriminating fluid connection between a source of fluid and a fluid receiving object, the tube set comprising medical tubing, a first connector in sealing connection with the tubing at a first end thereof, the first end of the tubing sealing with a first end of the connector, the first connector including at least one sealing surface and at least one non-sealing surface, the non-sealing surface being located closer to a free end of the first connector than the sealing surface, the non-sealing surface being sized and shaped for engaging a sealing surface of another connector simultaneously at least at three points and at a second end of the connector opposite the first end, each point being spaced at least 90 degrees from the other two points, the engagement between the non-sealing surface of the first connector and the sealing surface of said another connector preventing the formation of a fluid tight seal between the tubing and the source of fluid, the at least one non-sealing surface comprising at least one longitudinal channel in the connector at the second end of the connector, the channel having a length greater than a width of the sealing surface of said another connector that prevents the fluid tight seal with the sealing surface, the at least one longitudinal channel having a closed bottom located for opposing the sealing surface of said another connector upon engagement of the first connector with said another connector.

2. The tube set of claim 1 wherein the at least one non-sealing surface has a larger diameter than the at least one sealing surface.

3. The tube set of claim 1 further comprising a hole extending through the closed bottom of the longitudinal channel and opening into an interior of the first connector allowing fluid to escape through the hole when the non-sealing surface of the first connector engages the sealing surface of said another connector.

4. The tube set of claim 1 further comprising a second connector connected to the tubing at a second end thereof opposite the first end of the tubing, the second connector having at least one sealing member.

5. The tube set of claim 4 wherein the second connector comprises a receptacle including an inner end, an open outer end, and a sealing member located in the receptacle nearer to the open outer end.

6. The tube set of claim 1 in combination with a controller for controlling the supply of fluid from a source of pressurized fluid to a compression therapy device, the tube set being adapted to connect to the controller at a first end of the tube set, the controller comprising a housing and a fluid port in the housing for communicating with the first end of the tube set, the compression therapy device comprising the tube set, controller and at least one bladder.

7. A system for providing vascular compression comprising a controller, a tube set, and a compression therapy device, the controller including a first connector having at least one sealing surface and at least one non-sealing surface, the non-sealing surface being located closer to a free end of the first connector than the sealing surface, the compression therapy device including a second connector including a sealing member, the tube set including medical tubing and a third connector at a first end of the tubing having a sealing member adapted to engage the non-sealing surface and sealing surface of the first connector of the controller upon connection of the first and third connectors, and a fourth connector in sealing connection at a first end of the fourth connector with a second end of the tubing, the fourth connector having at least one sealing surface and at least one non-sealing surface located closer to a free end of the fourth connector than the sealing surface, the non-sealing surface of the fourth connector being adapted to engage the sealing member of the second connector at a second end of the fourth connector opposite the first end upon connection of the second and fourth connectors, the engagement between the non-sealing surface of the fourth connector and the sealing member of the second connector preventing the formation of a fluid tight seal between the compression device and the tubing, the at least one non-sealing surface of the fourth connector comprising at least one longitudinal channel in the fourth connector at the second end of the fourth connector, the channel having a length greater than a width of the sealing member of the second connector that prevents the fluid tight seal with the sealing member, the at least one longitudinal channel having a closed bottom located for opposing the sealing member of the second connector upon engagement of the fourth connector with the second connector.

8. A method of connecting a first device to a second device, comprising the steps of:
providing a first device having a first connector, the first connector including an attachment portion and a coupling portion, wherein the coupling portion includes a sealing surface at a second end and a non-sealing surface at a first end, the non-sealing surface defining an outermost diameter of the first connector;
providing a second device having a second connector, the second connector including a sealing member configured to receive the coupling portion, the sealing member defining an innermost diameter of the second connector less than the outermost diameter of the first connector;
attaching the first connector to the second connector; and
positioning the first and second connectors such that the sealing member of the second connector engages the non-sealing surface of the first connector preventing the formation of a fluid tight seal between the first and second devices, the sealing surface of the coupling portion then contacting the sealing member of the second connector forming a fluid tight seal between the first and second devices.

9. The method of claim 8 wherein the coupling portion includes a key located on the first connector;
the second connector having a housing having a mating cavity formed therein for capturing the key of the first connector when the first and second connectors are mated in sealing relation.

10. The method of claim 8 wherein the first connector has a housing and the coupling portion includes at least three substantially straight sides; and
the second connector having a housing defining a receptacle for receiving the first connector having at least three substantially straight sides shaped in correspondence with the shape of the first connector, the housing of the second connector further defining the non-sealing surface at an open end of the receptacle, the non-sealing surface flaring outwardly toward the end of the housing of the second connector and having at least one channel therein for inhibiting fluid-tight sealing engagement with the non-sealing surface.

11. A connector apparatus comprising:
a first connector having an attachment portion and a coupling portion, the coupling portion having at least one sealing surface and at least one non-sealing surface, the non-sealing surface defining an outermost diameter of the first connector; and
a second connector having an attachment portion and at least one sealing member and configured to receive the coupling portion, the sealing member defining an innermost diameter of the second connector less than the outermost diameter of the first connector, wherein during connection of the connectors the at least one sealing member first engages the at least one non-sealing surface preventing the formation of a fluid tight seal between the connectors, the at least one sealing member then sliding beyond the at least one non-sealing surface and contacting the sealing surface to create a fluid tight seal between the connectors.

12. The connector apparatus of claim 11 wherein the coupling portion includes a key located on the first connector;
the second connector having a housing having a mating cavity formed therein for capturing the key of the first connector when the first and second connectors are mated in sealing relation.

13. The connector apparatus of claim 11 wherein the first connector has a housing and the coupling portion including at least three substantially straight sides; and
the second connector having a housing defining a receptacle for receiving the first connector having at least three substantially straight side shaped in correspondence with the shape of the first connector, the housing of the second connector further defining the non-sealing surface at an open end of the receptacle, the non-sealing surface flaring outwardly toward the end of the housing of the second connector and having at least one channel therein for inhibiting fluid-tight sealing engagement with the non-sealing surface.

* * * * *